US011933796B2

(12) United States Patent
Fujimoto et al.

(10) Patent No.: US 11,933,796 B2
(45) Date of Patent: Mar. 19, 2024

(54) QUALITY CONTROL METHOD, QUALITY CONTROL SYSTEM, MANAGEMENT APPARATUS, ANALYZER, AND QUALITY CONTROL ABNORMALITY DETERMINATION METHOD

(71) Applicant: SYSMEX CORPORATION, Kobe (JP)

(72) Inventors: Keiji Fujimoto, Kobe (JP); Kazuhiko Matsuoka, Kobe (JP); Yasushi Hasui, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 0 days.

(21) Appl. No.: 17/750,040

(22) Filed: May 20, 2022

(65) Prior Publication Data

US 2022/0276273 A1  Sep. 1, 2022

Related U.S. Application Data

(60) Division of application No. 16/524,423, filed on Jul. 29, 2019, now Pat. No. 11,340,242, which is a continuation of application No. PCT/JP2018/000485, filed on Jan. 11, 2018.

(30) Foreign Application Priority Data

Jan. 31, 2017 (JP) .................. 2017-016383

(51) Int. Cl.
*G01N 35/00* (2006.01)
*G01N 15/14* (2006.01)
*G01N 33/487* (2006.01)
*G16H 10/40* (2018.01)
*G01N 15/10* (2006.01)
*G06F 17/00* (2019.01)
*G16B 50/00* (2019.01)

(52) U.S. Cl.
CPC ....... *G01N 35/00663* (2013.01); *G01N 15/14* (2013.01); *G01N 15/1429* (2013.01); *G01N 33/48792* (2013.01); *G01N 35/00613* (2013.01); *G01N 35/00623* (2013.01); *G01N 35/00871* (2013.01); *G16H 10/40* (2018.01); *G01N 2015/1068* (2013.01); *G01N 2015/1486* (2013.01); *G01N 2035/00653* (2013.01); *G01N 2035/00673* (2013.01); *G01N 2035/00683* (2013.01); *G06F 17/00* (2013.01); *G16B 50/00* (2019.02)

(58) Field of Classification Search
CPC ............. G01N 35/00663; G01N 15/14; G01N 15/1429; G01N 35/00613; G01N 35/00623; G01N 35/00871; G16H 10/40
See application file for complete search history.

(56) References Cited

U.S. PATENT DOCUMENTS

| | | | |
|---|---|---|---|
| 4,858,154 | A | 8/1989 | Anderson et al. |
| 5,532,941 | A | 7/1996 | Lin |
| 5,835,384 | A | 11/1998 | Lin |
| 11,340,242 | B2 | 5/2022 | Fujimoto |
| 2002/0128801 | A1 | 9/2002 | Okuno et al. |
| 2006/0105359 | A1 | 5/2006 | Favuzzi |
| 2007/0217949 | A1 | 9/2007 | Mimura |
| 2008/0021572 | A1 | 1/2008 | Yamaguchi et al. |
| 2008/0114559 | A1 | 5/2008 | Yamaguchi |
| 2009/0074618 | A1 | 3/2009 | Mizumoto |
| 2009/0199052 | A1 | 8/2009 | Yamaguchi et al. |
| 2009/0244068 | A1 | 10/2009 | Ikeda |
| 2013/0080082 | A1 | 3/2013 | Howes |
| 2015/0161552 | A1 | 6/2015 | Yamaguchi |
| 2016/0356801 | A1 | 12/2016 | Glavina et al. |

FOREIGN PATENT DOCUMENTS

| | | |
|---|---|---|
| CN | 101038293 A | 9/2007 |
| CN | 102141571 A | 8/2011 |
| CN | 102265163 A | 11/2011 |
| CN | 102866246 A | 1/2013 |
| CN | 103364572 A | 10/2013 |
| CN | 104075981 A | 10/2014 |
| CN | 104212872 A | 12/2014 |
| CN | 105807072 A | 7/2016 |
| JP | S63-503088 | 11/1988 |

(Continued)

OTHER PUBLICATIONS

Chinese Office Action dated Oct. 10, 2022, in a counterpart Chinese patent application No. 201880009083.7.
Communication pursuant to Article 94(3) EPC dated Nov. 17, 2022, in a counterpart European patent application No. 18748803.6.
Translation of JP-2008112465-A, Yamaguchi, Tadayuki, May 15, 2008 (Year:2008).
I. Inaoka et al., "External Quality Control of Clinical Examination with Network", Proceedings of the 17th Annual Conference of the Medical Informatics Association, Nov. 25, 1997, pp. 546-547, Japaneses Medical Informatics Association, Japan.

(Continued)

*Primary Examiner* — Jerry Lin
(74) *Attorney, Agent, or Firm* — Crowell & Moring LLP

(57) ABSTRACT

Provided are a quality control method, a quality control system, a management apparatus, an analyzer, and a quality control abnormality determination method in which measurement results of both a quality control substance and a specimen are sufficiently utilized to improve the quality of quality control. The quality control method used in a management apparatus which is connected via a network to an analyzer installed in each of a plurality of facilities includes obtaining, from an analyzer in each facility via a network, first quality control information obtained by measuring an artificially generated quality control substance, and second quality control information obtained by measuring a plurality of specimens by the analyzer in each facility; and outputting information concerning quality control of an analyzer in at least one facility, based on the obtained first quality control information and second quality control information.

22 Claims, 19 Drawing Sheets

(56) References Cited

FOREIGN PATENT DOCUMENTS

| | | |
|---|---|---|
| JP | H08-233825 | 9/1996 |
| JP | H9-502811 | 3/1997 |
| JP | 2003-279583 A | 10/2003 |
| JP | 2007-232510 A | 9/2007 |
| JP | 2012-248217 A | 12/2012 |
| JP | 2003-004750 | 1/2023 |
| JP | 2004-004105 | 1/2023 |
| JP | 2006-017600 | 1/2023 |
| JP | 2015-010939 | 1/2023 |
| JP | 2008-032751 | 2/2023 |
| JP | 2007-108136 | 4/2023 |
| JP | 2008-076267 | 4/2023 |
| JP | 2008-089609 | 4/2023 |
| JP | 2008112465 | 5/2023 |
| JP | 2009-181369 | 8/2023 |
| JP | 2007-248090 | 9/2023 |
| JP | 2009-243978 | 10/2023 |
| JP | 2014-194400 | 10/2023 |
| JP | 2014-202608 | 10/2023 |
| JP | 2007-292516 | 11/2023 |
| WO | WO-2014127285 | 8/2023 |

OTHER PUBLICATIONS

K.Ino, "About the external quality control sustems "eQAP"", Journal of the Japanese Society for Clinical Laboratory Automation, Aug. 1, 1999, vol. 24, (Total vol. 121), p. 417, Topic 93, Japan.

Japanese Office Action dated Aug. 18, 2020 in a counterpart Japanese patent application No. 2017-016383.

Kyoko Haraguchi et al: "Inter-Laboratory Comparison of CD34+ Cell Enumeration", The Japan Society of Transfusion Medicine and Cell Therapy, Japanese Journal of Transfusion and Cell Therapy, vol. 62, No. 1, 2016, pp. 32-40.

Kiyoshi Ichihara: "Practice of QC using patient data", Journal of Medical Technology, vol. 41, No. 4, Apr. 15, 1997, pp. 399-413.

Satoshi Nakayama: "Accuracy control of cell surface marker measurement in clinical laboratories", Cytometry Research 14(2), 2004, pp. 7-13.

Japanese Office Action dated Jan. 5, 2021 in a counterpart Japanese patent application No. 2017-016383.

Written Opinion dated Dec. 8, 2020 in a counterpart Singaporean patent application No. 11201906964T.

Extended European search report dated Sep. 1, 2020 and the Communication pursuant to Rules 70(2) and 70a(2) EPC issued on Sep. 18, 2020 in a counterpart European patent application No. 18748803.6.

Communication pursuant to Article 94(3) EPC dated Feb. 8, 2022 in a counterpart European patent application No. 18748803.6.

Examination Report dated Feb. 16, 2022 in a counterpart Australian patent application No. 2018216105.

Chinese Office Action with English Translation, dated Apr. 1, 2023, pp. 1-25, issued in a Chinese patent application No. 201880009083.7, China National Intellectual Property Administration, Beijing, China.

Rejection Decision dated May 27, 2023 in a counterpart Chinese patent application No. 201880009083.7.

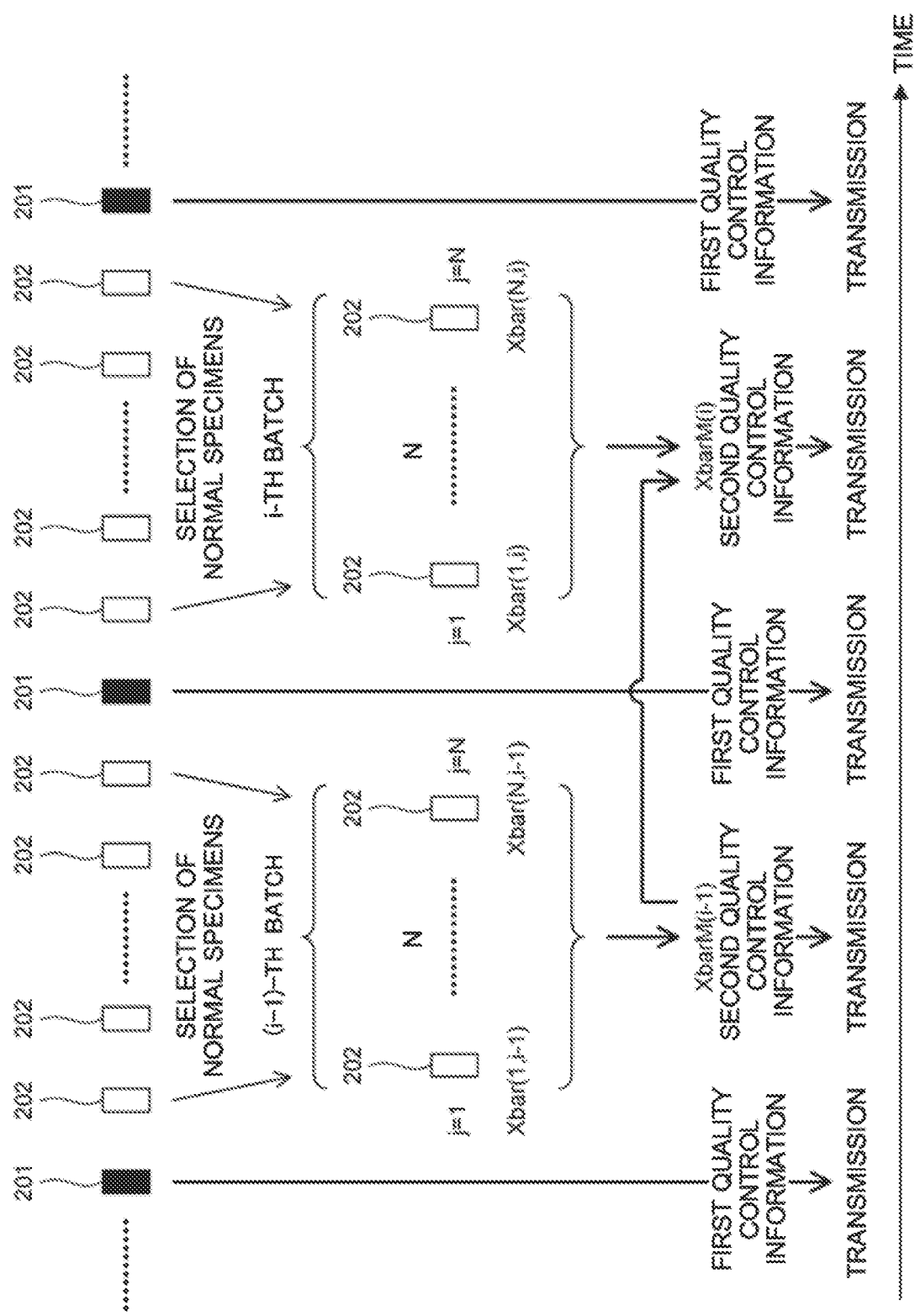

FIG. 6

$$XbarM(i) = XbarM(i-1)$$
$$+ SGN\left\{\sum_{j=1}^{N} SGN[Xbar(j,i) - XbarM(i-1)]\sqrt{|Xbar(j,i) - XbarM(i-1)|}\right\} \cdot F \quad \cdots (1)$$

$$F = \sqrt{\dfrac{\sum_{j=1}^{N} SGN[Xbar(j,i) - XbarM(i-1)]\sqrt{|Xbar(j,i) - XbarM(i-1)|}}{N}}^{\,2} \quad \cdots (2)$$

XbarM(i)   : i-TH BATCH XbarM
XbarM(i-1) : (i-1)-TH BATCH XbarM
Xbar(j,i)  : j-TH MEASUREMENT RESULT IN i-TH BATCH
SGN        : SIGN IN PARENTHESES (SIGNUM FUNCTION)
N          : THE NUMBER OF SAMPLES PER BATCH

QUALITY CONTROL METHOD, QUALITY CONTROL SYSTEM, MANAGEMENT APPARATUS, ANALYZER, AND QUALITY CONTROL ABNORMALITY DETERMINATION METHOD

CROSS REFERENCE TO RELATED APPLICATIONS

This application is a divisional of U.S. patent application Ser. No. 16/524,423, filed on Jul. 29, 2019, which is a continuation of International Application No. PCT/JP2018/000485, filed on Jan. 11, 2018, which claims priority to Japanese Patent Application No. 2017-016383, filed on Jan. 31, 2017. The disclosures of these applications are hereby incorporated by reference.

BACKGROUND OF THE INVENTION

1. Field of the Invention

The present invention relates to a quality control method, a quality control system, a management apparatus, an analyzer, and a quality control abnormality determination method for performing quality control of the analyzer.

2. Description of the Background Art

Japanese Laid-Open Patent Publication No. 2004-4105 discloses a system in which analyzers 402 disposed in facilities of a plurality of users, respectively, are connected to a management apparatus 401 via a network 403, as shown in FIG. 18. In this system, measurement results obtained by artificially generated quality control substances being measured by the respective analyzers 402, are transmitted to the management apparatus 401, and the management apparatus 401 compiles the measurement results, and provides the compiled result on a web page. The user in each of the facilities accesses the web page, and compares the measurement result from the analyzer 402 in the user's facility with the compiled result of all the facilities, to perform external quality control.

Japanese Laid-Open Patent Publication No. 2007-108136 discloses a quality control technique using a result of measurement of a quality control substance and a result of measurement of a specimen. As shown in FIG. 19, in a quality control system 500 disclosed in Japanese Laid-Open Patent Publication No. 2007-108136, a sample specimen and a quality control sample are supplied to a transport line 502 from a sample specimen supply unit 501 and a quality control sample supply unit 503. The sample specimen and the quality control sample are measured by an analyzer 504, and the measured sample specimen and quality control sample are collected by a sample specimen collection portion 506 and a quality control sample collection portion 505, respectively. A host computer 510 controls each component, and performs quality control for the analyzer based on the measurement results, from the analyzer 504, of the sample specimen and the quality control sample.

As disclosed in Japanese Laid-Open Patent Publication No. 2004-4105 and Japanese Laid-Open Patent Publication No. 2007-108136, while a plurality of techniques for quality control are known, a quality control substance is mainly used for quality control. Japanese Laid-Open Patent Publication No. 2007-108136 discloses the technique using a quality control substance and a specimen. However, since specimen properties may greatly vary depending on subjects from which specimens are collected, the measurement result greatly varies among specimens, and the measurement result of the specimen is not sufficiently used for quality control in practice.

SUMMARY OF THE INVENTION

Since the quality control is very important for assuring reliability of test results, the quality of the quality control is required to be improved by sufficiently utilizing measurement results of both a quality control substance and a specimen.

A first aspect of the present invention is directed to a quality control method used in a management apparatus (30) which is connected via a network (13) to an analyzer (20) installed in each of a plurality of facilities (12). The quality control method according to this aspect includes obtaining, from an analyzer (20) in each facility (12) via a network (13), first quality control information obtained by measuring an artificially generated quality control substance, and second quality control information obtained by measuring a plurality of specimens by the analyzer (20) in each facility (12); and outputting information concerning quality control of an analyzer (20) in at least one facility (12), based on the obtained first quality control information and second quality control information.

In the quality control method according to this aspect, the management apparatus can collect the first quality control information and the second quality control information that are obtained from the analyzer installed in each of the plurality of facilities. Therefore, for example, a staff member, in charge of a monitor, for an analyzer is allowed to appropriately evaluate the state of the quality control of the analyzers in the management apparatus. Furthermore, the present inventors have newly found that variation of the second quality control information is substantially small for a predetermined item, and found that the state of the quality control of the analyzer can be accurately evaluated by referring to the second quality control information for this item. Therefore, a state of the analyzer can be more appropriately and accurately evaluated by outputting the information concerning quality control based on the first quality control information and the second quality control information. Accordingly, the measurement results of both a quality control substance and a specimen can be sufficiently utilized to improve the quality of quality control.

The "quality control substance" may include a wide range of artificially generated quality control substances such as latex particles that imitate particles contained in a specimen and a substance prepared by a predetermined component being extracted from a specimen collected from an animal. The information concerning quality control represents, for example, a screen on which both kinds of the quality control information can be compared, and a determination result of a quality control state based on both kinds of the quality control information. The information concerning the quality control is outputted, for example, by display on a display unit, outputting of a sound, and transmission to another device.

In the quality control method according to this aspect, statistical information, obtained by statistical processing of a plurality of measurement results which are obtained by measuring a plurality of specimens by the analyzer (20) in each facility (12), is obtained as the second quality control information via the network (13) from the analyzer (20) in each facility (12). Thus, since statistical processing of measurement results of a plurality of specimens is performed, even if statistical information obtained by the statistical processing is obtained via the network, the measurement result of each specimen can be inhibited from leaking to the outside. Therefore, a state of the quality control can be appropriately evaluated while the measurement result of each specimen is prevented from leaking to the outside.

In this case, the analyzer (20) includes an optical flow cytometer (54), and the measurement result includes an intensity of light obtained by measuring a specimen. Statistical information, obtained by statistical processing of intensities of light which are obtained by measuring a plurality of specimens by the flow cytometer (54), is obtained as the second quality control information. The present inventors have found that variation of the second quality control information is substantially reduced when statistical information obtained by statistical processing of intensities of light which are obtained from a plurality of specimens by the flow cytometer is obtained as the second quality control information. Therefore, a state of quality control can be more appropriately evaluated by outputting the statistical information obtained by statistical processing of intensities of light as a measurement result.

In this case, the measurement result further includes a particle count value, for each kind of particle in the specimen, which is calculated based on the intensity of the light, and the second quality control information includes first statistical information obtained by statistical processing of the intensities of the light and second statistical information obtained by statistical processing of the particle count values.

The information concerning the quality control is outputted based on the first statistical information included in the second quality control information, and the first quality control information. Variation of the second statistical information included in the second quality control information is greater than variation of the first statistical information included in the second quality control information. That is, reliability of the second statistical information included in the second quality control information is not high. Therefore, a user who evaluates the quality control is allowed to appropriately evaluate a state of the quality control by using the first statistical information included in the second quality control information, as described above.

In the quality control method according to this aspect, the specimen is stained by a dye from which fluorescence is generated by excitation light, and the intensity of the light represents an intensity of the fluorescence generated from the dye by which the specimen is stained. The quality control substance is artificially generated, and is generally stored in a certain usage period of time and used for the quality control, so that the quality control substance may be deteriorated over time in the usage period of time. Meanwhile, a fresh specimen is measured in order to assure accuracy of analysis. Reactivity of a dye from which fluorescence is generated is different according to a deterioration state of a sample to be dyed. Therefore, variation in reactivity of a specimen to a dye is less than variation in reactivity of the quality control substance to the dye. Thus, when fluorescence is used as light intensity for obtaining the first quality control information and the second quality control information, variation of the second quality control information can be substantially reduced as compared to variation of the first quality control information. Therefore, the state of the quality control can be appropriately evaluated by outputting the second quality control information.

In the quality control method according to this aspect, the analyzer (20) in each facility (12) selects a predetermined number of measurement results from among measurement results in a predetermined period of time, and performs statistical processing of the selected predetermined number of measurement results to calculate the second quality control information. The quality of the quality control information based on a specimen can be improved by selecting measurement results, of the specimens, which are appropriate to statistical processing to perform the statistical processing.

In the quality control method according to this aspect, a display unit (40) is caused to separately display, as the information concerning the quality control, a screen on which the first quality control information can be referred to and a screen on which the second quality control information can be referred to. Thus, the quality control state of the analyzer can be visually evaluated by displaying the two screens.

In the quality control method according to this aspect, a display unit (40) is caused to display, as the information concerning the quality control, a screen (310) on which each of the first quality control information and the second quality control information can be referred to. Thus, the quality control state of the analyzer can be visually evaluated on the screen on which the first quality control information and the second quality control information can be referred to. The display unit may not necessarily be the display unit of the management apparatus, and examples of the display unit include a display unit of another device in the facility in which the management apparatus is installed, and a display unit installed in a facility other than the facility in which the management apparatus is installed.

In this case, the second quality control information is chronologically displayed on the screen (310). Thus, a time at which the second quality control information is greatly changed can be recognized, and it can be determined that abnormality in quality control may have occurred at the time. Therefore, by determining how the first quality control information has been changed at that time and further grasping other information to be examined for the quality control as appropriate, abnormality in quality control and the cause thereof can be estimated and quality control can be appropriately performed.

In this case, both the first quality control information and the second quality control information are chronologically displayed on the screen (310). Thus, change of the second quality control information and change of the first quality control information can be compared on one screen. Therefore, by comparing the first quality control information and the second quality control information, whether or not abnormality in quality control may have occurred can be smoothly and simply determined.

In the quality control method according to this aspect, the display unit (40) is caused to display, as the information concerning the quality control, a graph representing a combination of the first quality control information and the second quality control information, in a coordinate space in which two axes represent the first quality control information and the second quality control information. Thus, the quality control can be smoothly evaluated by referring to the first quality control information and the second quality control information.

In the quality control method according to this aspect, the display unit (40) is caused to display a screen (330) on which the second quality control information obtained from the analyzer (20) in the one facility (12) can be compared with the second quality control information obtained from the analyzer (20) in another facility (12) different from the one facility (12). Thus, a degree of deviation of a state of the analyzer in one facility from a state of the analyzer in another facility can be recognized. Therefore, the analyzer in one facility can be adjusted so as to reduce deviation of the result of the quality control.

In the quality control method according to this aspect, when a relationship between the second quality control information obtained from the analyzer (20) in the one facility (12) and the second quality control information obtained from the analyzer (20) in another facility (12) different from the one facility (12) satisfies a predetermined condition, report information is outputted as the information concerning the quality control. Examples of the "report information" may include various kinds of information such as an image, sound, and vibration which can be recognized by an operator. Examples of the "report information" may include information indicating a condition satisfied by the quality control information.

In this case, when the second quality control information obtained from the analyzer (20) in the one facility (12) indicates values distributed in a region outside a predetermined range which is set based on the second quality control information obtained from the analyzer (20) in another facility (12) different from the one facility (12), the report information is outputted. By using this condition, it can be appropriately determined that abnormality in correctness of a measurement result from the analyzer may have occurred.

Furthermore, when a width of variation of the second quality control information obtained from the analyzer (20) in the one facility (12) is outside a predetermined width range which is set based on the second quality control information obtained from the analyzer (20) in another facility (12) different from the one facility (12), the report information is outputted. By using this condition, it can be appropriately determined that abnormality in precision of a measurement result from the analyzer may have occurred.

In the quality control method according to this aspect, when the second quality control information satisfies a predetermined condition, report information indicating that abnormality in quality control may have occurred is outputted as the information concerning the quality control. Thus, it can be appropriately determined that abnormality in quality control may have occurred in the analyzer. Therefore, whether or not abnormality in quality control has occurred can be smoothly checked.

In this case, when the second quality control information has a value outside a predetermined variation range, the report information is outputted. By using this condition, it can be appropriately determined that abnormality in quality control may have occurred in the analyzer.

The quality control method according to this aspect includes performing remote access to the analyzer (20) in one facility (12) via the network (13) to cause a display unit (40) to display a screen of the analyzer (20) when the second quality control information obtained from the analyzer (20) in the one facility (12) satisfies a predetermined condition. Thus, a state of the quality control of the analyzer can be directly confirmed without movement to a place in which the analyzer 20 is installed.

The quality control method according to this aspect further includes obtaining information for displaying an analysis result of a specimen used for generating the second quality control information when the second quality control information satisfies a predetermined condition, and causing a display unit (40) to display the analysis result based on the obtained information. Thus, the cause of occurrence of abnormality in quality control can be examined in detail.

In the quality control method according to this aspect, when the second quality control information satisfies a predetermined condition, report information indicating that abnormality in a reagent may have occurred is outputted as the information concerning the quality control. Thus, possibility of abnormality occurring in a reagent can be recognized.

In this case, the quality control method according to this aspect further includes obtaining measurement data obtained by measuring a specimen used for generating the second quality control information when the second quality control information satisfies a predetermined condition; and performing determination whether or not a reagent other than a genuine reagent is used, based on the obtained measurement data, as determination of the abnormality in the reagent. Thus, whether or not a reagent other than a genuine reagent is used can be appropriately determined.

The quality control method according to this aspect includes setting the condition for determining whether or not abnormality in quality control has occurred based on the second quality control information obtained from a plurality of the analyzers (20). Thus, a condition based on the characteristics of the analyzer can be set.

In the quality control method according to this aspect, the analyzer (20) includes an optical flow cytometer (54). The quality control method includes determining whether or not abnormality in quality control may have occurred by using a combination of statistical information and a measurement result, the statistical information being obtained by statistical processing of intensities of light which are obtained by measuring each of a plurality of specimens by the flow cytometer (54), and the measurement result being obtained by analyzing measurement data obtained by measuring a quality control substance. Thus, when statistical information based on intensities of light which are obtained from a plurality of specimens by the flow cytometer is obtained as the second quality control information, variation of the second quality control information is substantially reduced. Furthermore, when the measurement result that is obtained by analyzing measurement data obtained from a quality control substance is obtained as the first quality control information, variation of the first quality control information is substantially reduced. Therefore, by the two kinds of the quality control information being used in combination, whether or not abnormality in quality control may have occurred can be accurately determined.

In the quality control method according to this aspect, when the first quality control information is normal and the second quality control information satisfies a predetermined condition, report information indicating that abnormality in a reagent may have occurred is outputted as the information concerning the quality control. Thus, possibility of abnormality having occurred in a reagent can be recognized.

A second aspect of the present invention is directed to a quality control system (10). The quality control system (10) according to this aspect includes analyzers (20) installed in a plurality of facilities (12); and a management apparatus (30) connected to an analyzer (20) in each of the facilities (12) via a network (13).

The analyzer (20) transmits first quality control information obtained by measuring an artificially generated quality control substance, and second quality control information obtained by measuring a plurality of specimens, via the network (13), to the management apparatus (30). The management apparatus (30), based on the first quality control information and the second quality control information which have been received from the analyzer (20), outputs information concerning quality control of an analyzer (20) in at least one facility (12).

The quality control system according to this aspect allows the same effect as that of the first aspect to be obtained.

In the quality control system (10) according to this aspect, the analyzer (20) may transmit statistical information that is obtained by statistical processing of a plurality of measurement results obtained by measuring a plurality of specimens, as the second quality control information, via the network (13), to the management apparatus (30).

In this case, the measurement result includes an intensity of light obtained by measuring a specimen. The analyzer (20) may include an optical flow cytometer (54), and may transmit statistical information as the second quality control information to the management apparatus (30), the statistical information being obtained by statistical processing of intensities of light which are obtained by measuring a plurality of specimens, respectively, by the flow cytometer (54), and the management apparatus (30) may output the received statistical information.

In this case, the measurement result further includes a particle count value, for each kind of particle in the specimen, which is calculated based on the intensity of the light. The analyzer (20) may transmit, to the management apparatus (30), the second quality control information that includes first statistical information obtained by statistical processing of the intensities of the light, and second statistical information obtained by statistical processing of the particle count values, and the management apparatus (30) may output the information concerning the quality control, based on the first statistical information included in the received second quality control information, and the received first quality control information.

In the quality control system (10) according to this aspect, the analyzer (20) may stain a specimen by a dye from which fluorescence is generated by excitation light, and the intensity of the light may represent an intensity of the fluorescence generated from the dye by which the specimen is stained.

In the quality control system (10) according to this aspect, the analyzer (20) may select a predetermined number of measurement results from among measurement results in a predetermined period of time, and perform statistical processing of the selected predetermined number of measurement results, to calculate the second quality control information.

In the quality control system (10) according to this aspect, the management apparatus (30) may perform a process for causing a display unit (40) to separately display, as the information concerning the quality control, a screen on which the first quality control information can be referred to and a screen on which the second quality control information can be referred to.

In the quality control system (10) according to this aspect, the management apparatus (30) may perform a process for causing a display unit (40) to display, as the information concerning the quality control, a screen (310) on which each of the first quality control information and the second quality control information can be referred to.

In this case, the management apparatus (30) may perform a process for chronologically displaying the second quality control information on the screen (310).

In this case, the management apparatus (30) may perform a process for chronologically displaying, on the screen (310), both the first quality control information and the second quality control information.

In the quality control system (10) according to this aspect, the management apparatus (30) may perform a process for causing the display unit (40) to display, as the information concerning the quality control, a graph representing a combination of the first quality control information and the second quality control information, in a coordinate space in which two axes represent the first quality control information and the second quality control information.

In the quality control system (10) according to this aspect, the management apparatus (30) may perform a process for causing the display unit (40) to display a screen (330) on which the second quality control information obtained from the analyzer (20) in the one facility (12) can be compared with the second quality control information obtained from the analyzer (20) in another facility (12) different from the one facility (12).

In the quality control system (10) according to this aspect, the management apparatus (30) may perform a process for outputting report information as the information concerning the quality control when a relationship between the second quality control information obtained from the analyzer (20) in the one facility (12) and the second quality control information obtained from the analyzer (20) in another facility (12) different from the one facility (12) satisfies a predetermined condition.

In this case, the management apparatus (30) may perform a process for outputting the report information when the second quality control information obtained from the analyzer (20) in the one facility (12) indicates values distributed in a region outside a predetermined range which is set based on the second quality control information obtained from the analyzer (20) in another facility (12) different from the one facility (12).

Furthermore, the management apparatus (30) may perform a process for outputting the report information when a width of variation of the second quality control information obtained from the analyzer (20) in the one facility (12) is outside a predetermined width range which is set based on the second quality control information obtained from the analyzer (20) in another facility (12) different from the one facility (12).

In the quality control system (10) according to this aspect, when the second quality control information satisfies a predetermined condition, the management apparatus (30) may perform a process for outputting, as the information concerning the quality control, report information indicating that abnormality in quality control may have occurred.

In this case, the management apparatus (30) may perform a process for outputting the report information when the second quality control information has a value outside a predetermined variation range.

In the quality control system (10) according to this aspect, when the second quality control information obtained from the analyzer (20) in the one facility (12) satisfies a predetermined condition, the management apparatus (30) performs remote access to the analyzer (20) in the one facility (12), via the network (13), to perform a process for causing a display unit (40) to display a screen of the analyzer (20).

In the quality control system (10) according to this aspect, when the second quality control information satisfies a predetermined condition, the management apparatus (30) may further obtain information for displaying an analysis result of a specimen used for generating the second quality control information and perform a process for causing a display unit (40) to display the analysis result based on the obtained information.

In the quality control system (10) according to this aspect, when the second quality control information satisfies a predetermined condition, the management apparatus (30) may perform a process for outputting, as the information concerning the quality control, report information indicating that abnormality in a reagent may have occurred.

In this case, when the second quality control information satisfies a predetermined condition, the management apparatus (30) may further obtain measurement data obtained by measuring a specimen used for generating the quality control information, and may perform determination whether or not a reagent other than a genuine reagent is used, based on the obtained measurement data, as determination of the abnormality in the reagent.

In the quality control system (10) according to this aspect, the management apparatus (30) may set the condition for determining whether or not abnormality in quality control has occurred, based on the second quality control information obtained from a plurality of the analyzers (20).

In the quality control system (10) according to this aspect, the analyzer (20) may include an optical flow cytometer (54), and may transmit statistical information and a measurement result to the management apparatus (30), the statistical information being obtained by statistical processing of intensities of light which are obtained by measuring each of a plurality of specimens by the flow cytometer (54), and the measurement result being obtained by analyzing the measurement data which is obtained by measuring a quality control substance, and the management apparatus (30) may determine whether or not abnormality in quality control may have occurred, by using a combination of the received statistical information and measurement result.

In the quality control system (10) according to this aspect, when the first quality control information is normal and the second quality control information satisfies a predetermined condition, the management apparatus (30) may perform a process for outputting report information indicating that abnormality in a reagent may have occurred, as the information concerning the quality control.

A third aspect of the present invention is directed to a management apparatus (30). The management apparatus (30) according to this aspect includes obtaining first quality control information obtained by measuring an artificially generated quality control substance, and second quality control information obtained by measuring a plurality of specimens, via a network (13), from an analyzer (20) installed in each of a plurality of facilities (12); and outputting information concerning quality control of an analyzer (20) in at least one facility (12) based on the obtained first quality control information and second quality control information.

The management apparatus according to this aspect allows the same effect as that of the first aspect to be obtained.

A fourth aspect of the present invention is directed to an analyzer (20) connected to a management apparatus (30) via a network (13). The analyzer (20) according to this aspect includes a measurement unit (50) configured to measure a specimen; an analysis unit (61) configured to analyze measurement data obtained by the measurement unit (50); and a transmission unit (65) configured to transmit, to the management apparatus (30), an analysis result obtained by the analysis unit (61). The analysis unit (61) generates first quality control information based on the measurement data obtained by measuring an artificially generated quality control substance by the measurement unit (50), obtains a measurement result, for each specimen, based on the measurement data obtained by measuring a plurality of specimens by the measurement unit (50), and generates second quality control information based on the obtained measurement result of each specimen. The transmission unit (65) transmits, to the management apparatus (30), the first quality control information and the second quality control information generated by the analysis unit (61).

The analyzer according to this aspect allows the same effect as that of the first aspect to be obtained.

A fifth aspect of the present invention is directed to a quality control abnormality determination method. The quality control abnormality determination method according to this aspect determines abnormality of quality control in an analyzer (20) based on first quality control information obtained by measuring an artificially generated quality control substance, and second quality control information obtained by measuring a plurality of specimens.

The quality control abnormality determination method according to this aspect allows abnormality in quality control to be more accurately determined, as compared to a case where abnormality in quality control is determined based on either the first quality control information or the second quality control information In the quality control abnormality determination method according to this aspect, the second quality control information may be statistical information that is obtained by statistical processing of a plurality of measurement results obtained by measuring each of the plurality of specimens by the analyzer (20).

In the quality control abnormality determination method according to this aspect, the analyzer (20) may include an optical flow cytometer (54), the measurement result may include an intensity of light obtained by measuring a specimen, and the statistical information may be obtained by statistical processing of intensities of light which are obtained by measuring a plurality of specimens by the flow cytometer (54).

According to the present invention, measurement results from both a quality control substance and a specimen can be sufficiently utilized to improve the quality of quality control.

BRIEF DESCRIPTION OF THE DRAWINGS

FIG. 5 illustrates quality control information to be transmitted from an information processing unit to the management apparatus according to the embodiment;

FIG. 6 illustrates an equation for calculating XbarM according to the embodiment;

DETAILED DESCRIPTION OF THE PREFERRED EMBODIMENTS

Figure 1:
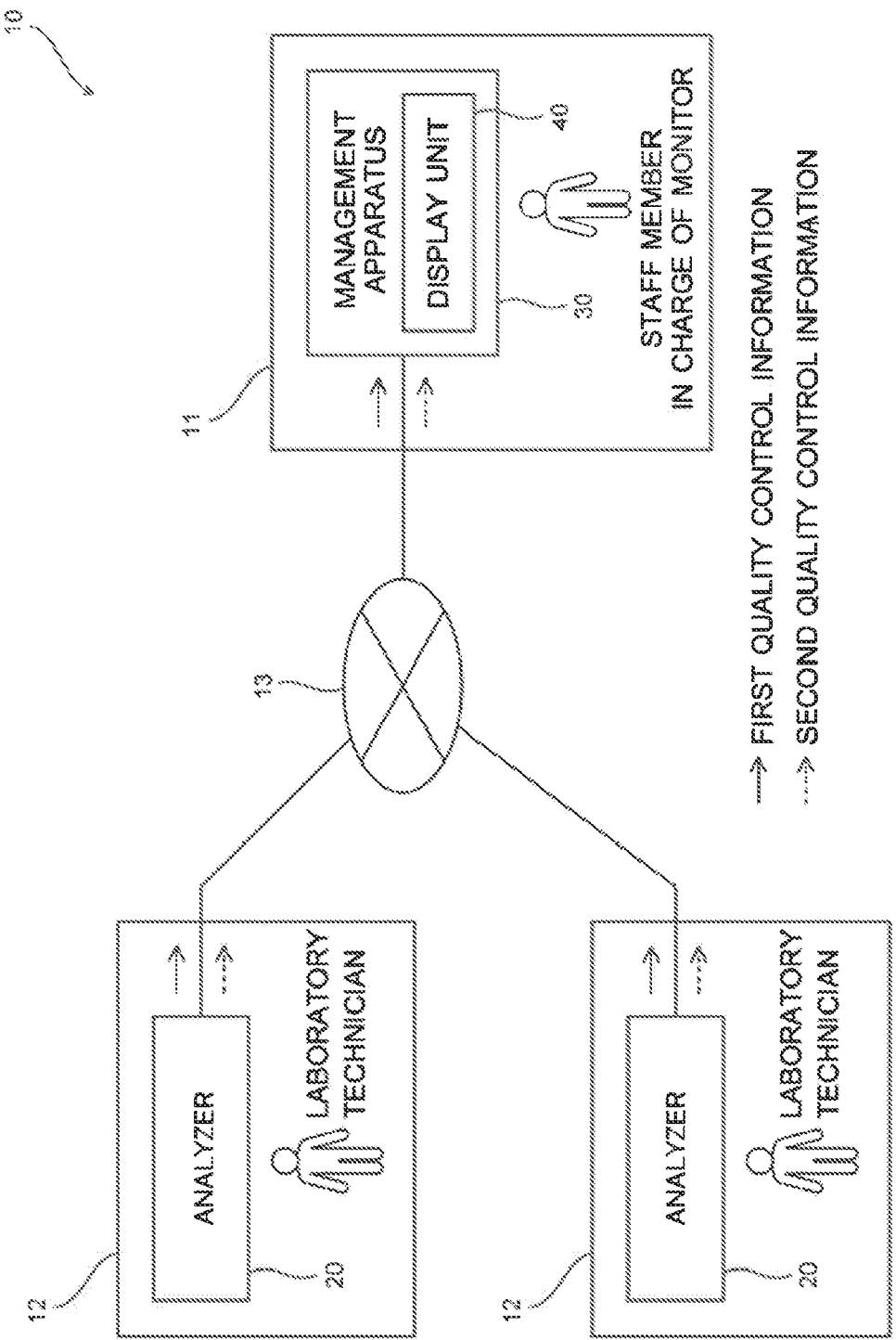
FIG. 1 is a block diagram illustrating a configuration of a quality control system according to an embodiment.

As shown in FIG. 1, a quality control system 10 includes an analyzer 20 and a management apparatus 30. The management apparatus 30 is installed in a facility 11 such as a customer support center. The analyzer 20 is installed in a facility 12 such as a hospital and a testing center. The facility 12 and the facility 11 are facilities different from each other. The analyzer 20 and the management apparatus 30 are connected to a network 13 such as the Internet, and can communicate with each other via the network 13. In the example shown in FIG. 1, the quality control system 10 includes a plurality of the facilities 12. Each of the plurality of the facilities 12 includes one or more analyzers 20.

One or more laboratory technicians are located in the facility 12 in general. The laboratory technician operates the analyzer 20 in the facility 12 in which the laboratory technician is located. The analyzer 20 measures an artificially generated quality control substance, and measures a specimen collected from a subject or a patient. The analyzer 20 analyzes measurement data obtained by the measurement and obtains a measurement result. The analyzer 20 transmits first quality control information obtained by measuring the quality control substance, and second quality control information obtained by measuring a plurality of specimens, to the management apparatus 30, via the network 13. The management apparatus 30 obtains the first quality control information and the second quality control information from the analyzers 20 of the facilities 12 via the network 13, and stores the first quality control information and the second quality control information.

The "quality control substance" may include a wide range of artificially generated quality control substances such as latex particles that imitate particles contained in a specimen and a substance prepared by a predetermined component being extracted from a specimen collected from an animal.

The management apparatus 30 outputs information concerning quality control of the analyzer 20 of at least one of the facilities 12, based on the first quality control information and the second quality control information that are obtained from the analyzers 20 and stored. The information concerning quality control represents, for example, a screen which allows comparison of the first quality control information and the second quality control information, and a result of determination of a quality control state based on the first quality control information and the second quality control information. The information concerning quality control is outputted by, for example, display on a display unit 40 of the management apparatus 30, by a sound from a speaker of the management apparatus 30, or by transmission to another device.

A staff member in charge of a monitor of the analyzer 20 is located in the facility 11. The staff member in charge of the monitor operates the management apparatus 30 and handles inquiries about the analyzer 20 from the laboratory technician. The management apparatus 30 causes the display unit 40 to display, for example, a screen on which the first quality control information and the second quality control information which are received from the analyzer 20 can be referred to. The staff member in charge of the monitor evaluates a state of the quality control of the analyzer 20 by referring to the screen displayed on the display unit 40.

Thus, according to the embodiment, the management apparatus 30 can collect the first quality control information and the second quality control information that are obtained from the analyzers 20 installed in the plurality of facilities 12, respectively. Therefore, the staff member in charge of the monitor on the management apparatus 30 side is allowed to appropriately evaluate the state of the quality control of the analyzer 20. As described below, the present inventors have found that variation of the second quality control information obtained by measuring a plurality of specimens is substantially small for a predetermined item, and found that the state of the quality control of the analyzer 20 can be accurately evaluated by referring to the second quality control information for this item. Therefore, a quality control state of the analyzer 20 can be more appropriately and accurately evaluated by outputting the information concerning quality control based on the first quality control information and the second quality control information. Accordingly, the measurement results of both a quality control substance and a specimen can be sufficiently utilized to improve the quality of quality control.

Figure 2:
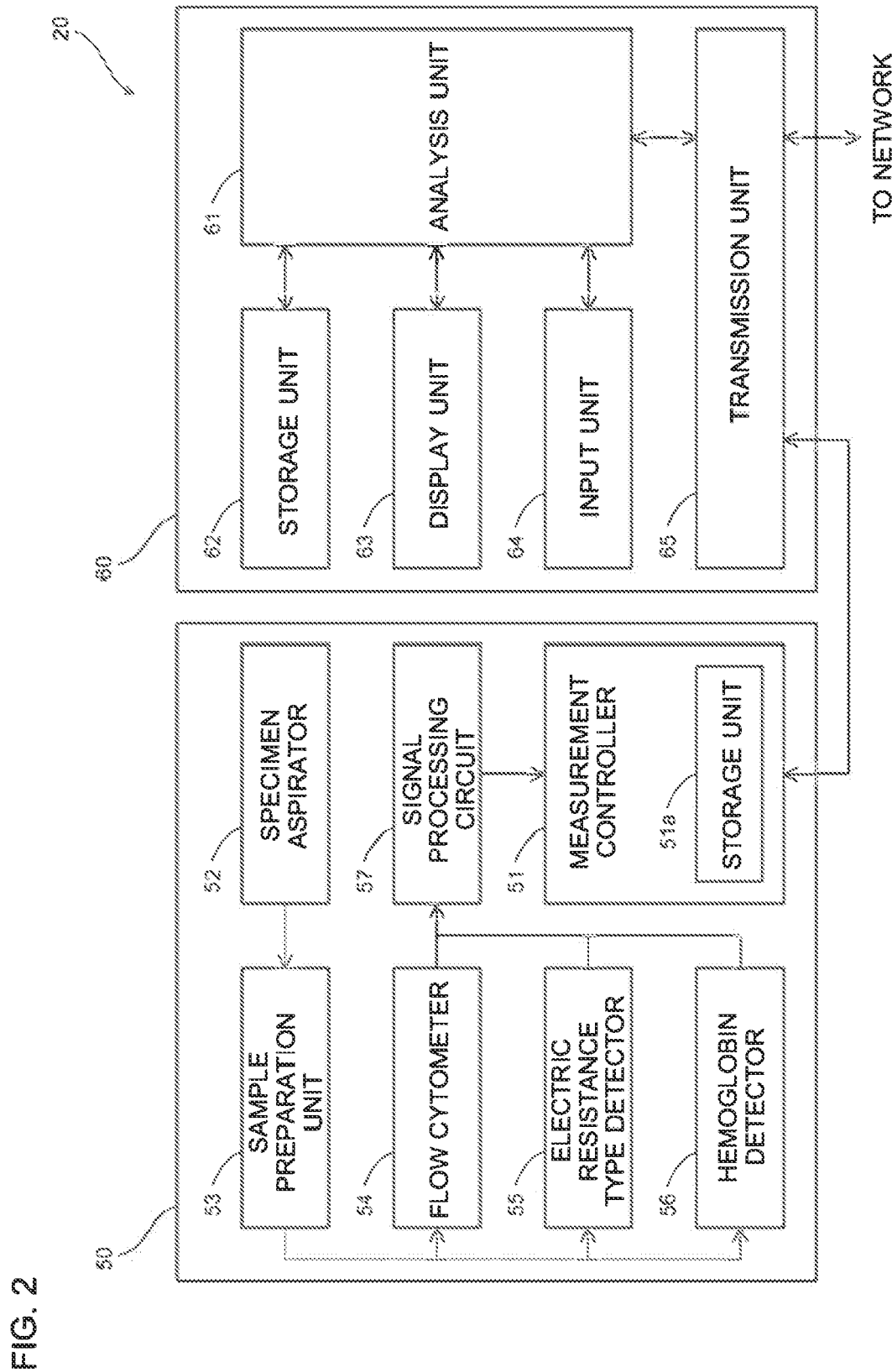
FIG. 2 is a block diagram illustrating a configuration of an analyzer according to the embodiment.

As shown in FIG. 2, the analyzer 20 includes a measurement unit 50 and an information processing unit 60.

The measurement unit 50 includes a measurement controller 51, a specimen aspirator 52, a sample preparation unit 53, a flow cytometer 54, an electric resistance type detector 55, a hemoglobin detector 56, and a signal processing circuit 57.

The measurement controller 51 is implemented by, for example, a CPU and a MPU. The measurement controller 51 receives a signal outputted by each of components of the measurement unit 50, and controls the components of the measurement unit 50. The measurement controller 51 communicates with the information processing unit 60. The measurement controller 51 includes a storage unit 51a. The storage unit 51a is implemented by, for example, a ROM, a RAM, a hard disk, or the like. The measurement controller 51 performs processing based on a program stored in the storage unit 51a. The specimen aspirator 52 has a not-illustrated aspirating tube, and aspirates a specimen stored in a specimen container and a quality control substance stored in a container, by way of the aspirating tube. The specimen of the embodiment is peripheral whole blood collected from a subject.

A plurality of containers which store a plurality of reagents, respectively, used for measurement are connected to the sample preparation unit 53. The sample preparation unit 53 mixes a specimen and a predetermined reagent with each other to prepare a measurement sample for counting of white blood cells, and classification and counting of basophils and nucleated red blood cells. Hereinafter, the measurement sample is referred to as "WNR measurement sample". The sample preparation unit 53 mixes a specimen and a predetermined reagent with each other to prepare a measurement sample for classification and counting of neutrophils, lymphocytes, monocytes, and eosinophils, and detection of abnormal cells such as immature white blood cells and atypical lymphocytes. Hereinafter, the measurement sample is referred to as "WDF measurement sample". The sample preparation unit 53 mixes a specimen and a predetermined reagent with each other to prepare a measurement sample for classification and counting of reticulocytes. Hereinafter, the measurement sample is referred to as "RET measurement sample". The sample preparation unit 53 mixes a specimen and a predetermined reagent with each other to prepare a measurement sample for detection of blast cells and abnormal lymphocytic cells. Hereinafter, the measurement sample is referred to as "WPC measurement sample". The reagents used for preparing the WNR measurement sample, the WDF measurement sample, the RET measurement sample, and the WPC measurement sample each contain a dye from which fluorescence is generated by excitation light.

The sample preparation unit 53 mixes a specimen and a predetermined reagent with each other to prepare a measurement sample for counting of red blood cells and platelets. Hereinafter, the measurement sample is referred to as "RBC/PLT measurement sample". The sample preparation unit 53 mixes a specimen and a predetermined reagent with each other to prepare a measurement sample for measurement of a hemoglobin concentration. Hereinafter, the measurement sample is referred to as "HGB measurement sample".

The sample preparation unit 53 mixes, similarly to the specimen, a quality control substance and a predetermined reagent with each other to prepare a WNR measurement sample, a WDF measurement sample, a RET measurement sample, a WPC measurement sample, a RBC/PLT measurement sample, and an HGB measurement sample.

The WNR measurement sample, the WDF measurement sample, the RET measurement sample, and the WPC measurement sample are sent to the flow cytometer 54, and measured by the flow cytometer 54. The RBC/PLT measurement sample is sent to the electric resistance type detector 55, and measured by the electric resistance type detector 55. The HGB measurement sample is sent to the hemoglobin detector 56, and measured by the hemoglobin detector 56.

Figure 3:
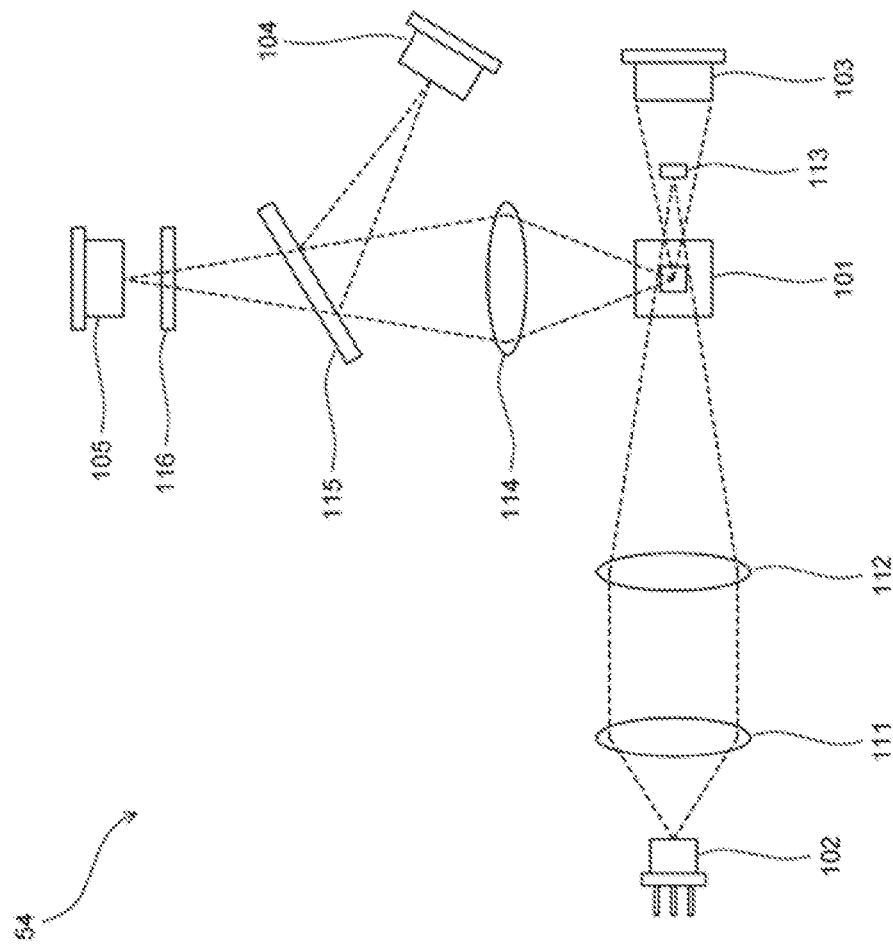
FIG. 3 schematically illustrates a configuration of a flow cytometer according to the embodiment.

As shown in FIG. 3, the flow cytometer 54 is an optical flow cytometer that measures blood cells by using a flow cytometry method. The flow cytometer 54 includes a flow cell 101, a light source 102, light receivers 103, 104, and 105, a collimator lens 111, a condenser lens 112, a beam stopper 113, a condenser lens 114, a dichroic mirror 115, and an optical filter 116.

The WNR measurement sample, the WDF measurement sample, the RET measurement sample, and the WPC measurement sample are separately supplied to the flow cell 101 when measurement is performed. The flow cell 101 is formed from a translucent material into a tubular shape. Each measurement sample flows in the flow cell 101 in a state where the measurement sample is surrounded by a sheath liquid. Thus, particles contained in each measurement sample flow through the flow cell 101 in a state where the particles are aligned in a line. The light source 102 is a semiconductor laser light source, and emits laser light having a predetermined wavelength. The light emitted from the light source 102 is excitation light that excites a dye contained in each measurement sample, and causes fluorescence in a predetermined wavelength band to be generated from the dye.

The collimator lens 111 and the condenser lens 112 condense light emitted from the light source 102, to apply the light to each measurement sample that flows in the flow cell 101. When the light from the light source 102 is applied to the measurement sample, forward scattered light, side scattered light, and fluorescence are generated from the particle in the measurement sample. The forward scattered light represents information concerning the size of the particle. The side scattered light represents information of the inside of the particle. The fluorescence represents a degree of staining of the particle. Of light applied to the flow cell 101, light that has not been applied to the particle and has been transmitted through the flow cell 101 is blocked by the beam stopper 113. The light receiver 103 is implemented by, for example, a photodiode. The light receiver 103 receives the forward scattered light and outputs an electrical signal based on the received forward scattered light.

The condenser lens 114 condenses the fluorescence and the side scattered light that have been generated on the side of the flow cell 101. The dichroic mirror 115 reflects the side scattered light condensed by the condenser lens 114, and transmits the fluorescence condensed by the condenser lens 114 therethrough. The light receiver 104 is implemented by, for example, a photodiode. The light receiver 104 receives the side scattered light reflected by the dichroic mirror 115, and outputs an electrical signal based on the received side scattered light. Of the light that has been transmitted through the dichroic mirror 115, the optical filter 116 transmits only fluorescence to be received by the light receiver 105 therethrough. The light receiver 105 is implemented by, for example, an avalanche photodiode. The light receiver 105 receives the fluorescence that has been transmitted through the optical filter 116 and outputs an electrical signal based on the received fluorescence.

Returning to FIG. 2, the electric resistance type detector 55 measures blood cells by using a sheath flow DC detection method. The RBC/PLT measurement sample is supplied to a not-illustrated flow cell of the electric resistance type detector 55 when the measurement is performed. The electric resistance type detector 55 applies voltage to the RBC/PLT measurement sample that flows in the flow cell of the electric resistance type detector 55, and detects change of the voltage which is caused by passing of particles, to detect the particles. The electric resistance type detector 55 outputs a detection signal.

The hemoglobin detector 56 measures hemoglobin by an SLS-hemoglobin method. The HGB measurement sample is supplied to a not-illustrated cell of the hemoglobin detector 56 when the measurement is performed. The hemoglobin detector 56 applies light to the HGB measurement sample stored in the cell of the hemoglobin detector 56, and detects an absorbance based on the HGB measurement sample. The hemoglobin detector 56 outputs a detection signal.

The signal processing circuit 57 performs signal processing of the signals outputted from the light receivers 103 to 105. Specifically, the signal processing circuit 57 extracts waveforms corresponding to the particles based on the signals outputted from the light receivers 103 to 105, and calculates a peak value, a width, an area, and the like of the waveform for each particle. Hereinafter, the peak values of the waveforms based on the signals outputted from the light receivers 103 to 105 are referred to as "forward scattered light intensity", "side scattered light intensity", and "fluorescence intensity", respectively. Each of the forward scattered light intensity, the side scattered light intensity, and the fluorescence intensity may be represented by a width or an area of the waveform.

The signal processing circuit 57 extracts waveforms corresponding to particles based on the signals outputted from the electric resistance type detector 55, and calculates a peak value of the waveform for each particle. The signal processing circuit 57 calculates a hemoglobin concentration based on the signal outputted from the hemoglobin detector 56.

The signal processing circuit 57 obtains measurement data by performing the above-described signal processing of the signals outputted from the flow cytometer 54, the electric resistance type detector 55, and the hemoglobin detector 56, and outputs the obtained measurement data to the measurement controller 51.

The measurement controller 51 stores, in the storage unit 51a, the measurement data outputted from the signal processing circuit 57. When the measurements of the specimen and the quality control substance have ended, the measurement controller 51 transmits the measurement data stored in the storage unit 51a, to the information processing unit 60. The "measurement data" represents data that is obtained by the signal processing circuit 57 and transmitted from the measurement unit 50 to the information processing unit 60.

The information processing unit 60 includes an analysis unit 61, a storage unit 62, a display unit 63, an input unit 64, and a transmission unit 65.

The analysis unit 61 is implemented by, for example, a CPU. The analysis unit 61 receives a signal outputted by each of components of the information processing unit 60, and controls the components of the information processing unit 60. The analysis unit 61 communicates with the measurement unit 50 via the transmission unit 65. The analysis unit 61 communicates with the management apparatus 30 via the transmission unit 65 and the network 13. The storage unit 62 is implemented by, for example, a ROM, a RAM, a hard disk, or the like. The analysis unit 61 performs processing based on a program stored in the storage unit 62.

The display unit 63 is implemented by, for example, a display. The display unit 63 displays a screen on which an analysis result is indicated. The input unit 64 is implemented by, for example, a mouse or a keyboard. The input unit 64 receives input from a laboratory technician. The display unit 63 and the input unit 64 may be integrated as a touch panel or the like. The transmission unit 65 is implemented by, for example, a network interface card. The transmission unit 65 outputs, to the analysis unit 61, information received from another device, and transmits, to another device, information outputted by the analysis unit 61.

The analysis unit 61 stores, in the storage unit 62, the measurement data received from the measurement unit 50. The analysis unit 61 generates an analysis result as described below, based on the measurement data received from the measurement unit 50.

The analysis unit 61 performs analysis such as classification and counting of blood cells, based on the measurement data of a specimen, and calculates measurement results for a plurality of measurement items. The analysis unit 61 performs analysis such as classification and counting of particles, similarly to the analysis of blood cells, based on the measurement data of a quality control substance, and calculates measurement results for a plurality of measurement items. The measurement items include so-called CBC items such as the number of white blood cells, the number of red blood cells, the number of platelets, an amount of hemoglobin, a hematocrit value, a mean corpuscular volume, a mean corpuscular hemoglobin, and a mean corpuscular hemoglobin concentration.

The analysis unit 61 calculates, as measurement results, one forward scattered light intensity, one side scattered light intensity, and one fluorescence intensity, from the forward scattered light intensities, the side scattered light intensities, and the fluorescence intensities which are included in the measurement data. For example, in the case of the WNR measurement sample, a plurality of forward scattered light intensities corresponding to the number of particles are obtained by the measurement. The analysis unit 61 calculates a median of the plurality of forward scattered light intensities included in the measurement data, and sets the calculated median as the one forward scattered light intensity. Similarly, the analysis unit 61 calculates a median of a plurality of side scattered light intensities obtained from the WNR measurement sample, and a median of a plurality of fluorescence intensities obtained from the WNR measurement sample, and sets the calculated medians as the one side scattered light intensity and the one fluorescence intensity. The analysis unit 61 performs the processing as described above for the WNR measurement sample, the WDF measurement sample, the RET measurement sample, and the WPC measurement sample which are based on the quality control substance, and performs the processing as described above for the WNR measurement sample, the WDF measurement sample, the RET measurement sample, and the WPC measurement sample which are based on the specimen. A mean value may be used instead of the median.

Thus, the analysis unit 61 calculates, as the measurement results, one forward scattered light intensity, one side scattered light intensity, and one fluorescence intensity, based on the light intensities included in the measurement data of each of the specimen and the quality control substance. Hereinafter, the one light intensity calculated as described above is referred to as "sensitivity item". The sensitivity items include one forward scattered light intensity, one side scattered light intensity, and one fluorescence intensity for each of the WNR measurement sample, the WDF measurement sample, the RET measurement sample, and the WPC measurement sample.

The analysis unit 61 performs statistical processing of the measurement results, for the measurement items, based on a plurality of specimens to obtain statistical information, and performs statistical processing of the measurement results, for the sensitivity items, based on a plurality of specimens to obtain statistical information. The statistical information will be described below with reference to FIGS. 5 and 6.

The "measurement result" represents a numerical value calculated for each measurement item, and a numerical value calculated for each sensitivity item. The "analysis result" conceptually includes the measurement result, a scattergram associated with calculation of the measurement result, and statistical information obtained by statistical processing of the measurement results.

The analysis unit 61 transmits the measurement results of the measurement items based on the quality control substance and the measurement results of the sensitivity items based on the quality control substance, as the first quality control information, to the management apparatus 30 via the network 13. The analysis unit 61 transmits the statistical information of the measurement items based on a plurality of specimens and the statistical information of the sensitivity items based on a plurality of specimens, as the second quality control information, to the management apparatus 30 via the network 13.

In a case where the statistical processing of the measurement results based on the plurality of specimens is performed as described above, even if the statistical information obtained by the statistical processing is transmitted via the network 13, the measurement results of each specimen can be inhibited from leaking to the outside. Therefore, the state of the quality control of the analyzer 20 can be appropriately evaluated by the management apparatus 30 while the measurement results of each specimen are prevented from leaking to the outside.

The analysis unit 61 transmits device information in addition to the first quality control information and the second quality control information via the network 13 to the management apparatus 30. The device information includes, for example, a name of a facility, a facility number, an analyzer number, a type of the analyzer, a name of a reagent, a reagent lot, a name of a quality control substance, a quality control substance lot, date and time, and a device temperature.

Figure 4:
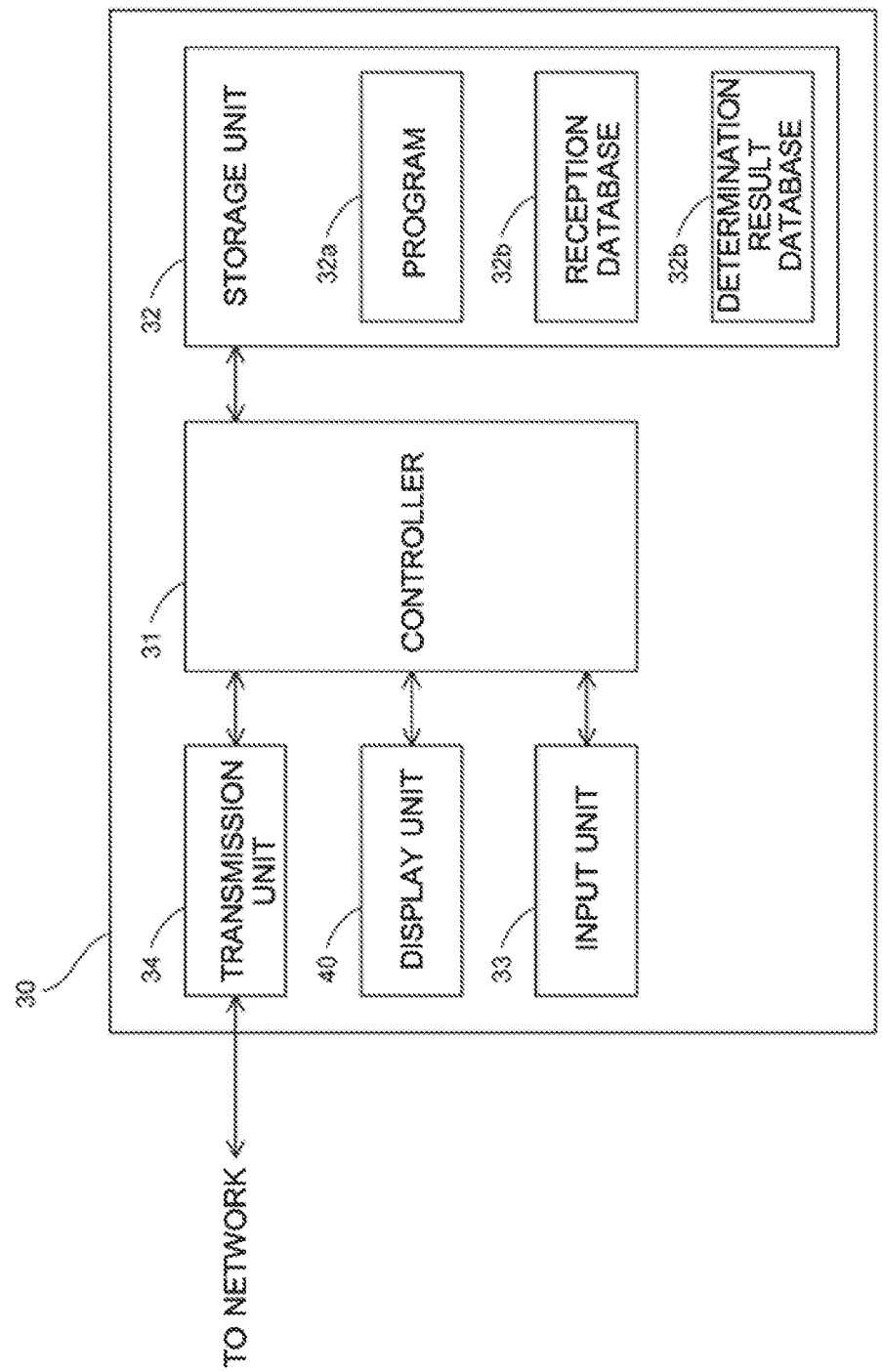
FIG. 4 is a block diagram illustrating a configuration of a management apparatus according to the embodiment.

As shown in FIG. 4, the management apparatus 30 includes a controller 31, a storage unit 32, an input unit 33, a transmission unit 34, and the display unit 40.

The controller 31 is implemented by, for example, a CPU. The controller 31 receives a signal outputted by each of components of the management apparatus 30, and controls the components of the management apparatus 30. The controller 31 communicates with the information processing unit 60 of the analyzer 20 via the network 13. The storage unit 32 is implemented by, for example, a ROM, a RAM, a hard disk, or the like. The storage unit 32 stores a program 32a, a reception database 32b, and a determination result database 32c. The controller 31 performs processing based on the program 32a stored in the storage unit 32.

The reception database 32b stores the first quality control information, the second quality control information, and the device information which are transmitted from each analyzer 20. The determination result database 32c includes the result of determination as to abnormality in quality control. Conditions under which it is determined that quality control is abnormal are stored in the storage unit 32.

The display unit 40 is implemented by, for example, a display. The input unit 33 is implemented by, for example, a mouse or a keyboard. The display unit 40 and the input unit 33 may be integrated as a touch panel or the like. The transmission unit 34 is implemented by, for example, a network interface card. The transmission unit 34 outputs, to the controller 31, information received from another device, and transmits, to another device, information outputted from the controller 31.

Next, the quality control information transmitted from the information processing unit 60 to the management apparatus 30 will be described with reference to FIG. 5.

As described above, the analysis unit 61 of the information processing unit 60 calculates measurement results of the measurement items based on a quality control substance, and measurement results of the sensitivity items based on the quality control substance. The analysis unit 61 calculates statistical information by performing statistical processing of measurement results, of the measurement items, based on a plurality of specimens, and calculates statistical information by performing statistical processing of measurement results, of the sensitivity items, based on the plurality of specimens.

In FIG. 5, a measurement result group 201 includes measurement results, of the measurement items and the sensitivity items, which are obtained from one quality control substance. A measurement result group 202 includes measurement results, of the measurement items and the sensitivity items, which are obtained from one specimen. The quality control substance is measured at predetermined time intervals. Specimens are measured between the measurements of the quality control substances. Therefore, as shown in FIG. 5, the measurement result groups 201 and 202 are chronologically arranged, and a plurality of the measurement result groups 202 are arranged between the two measurement result groups 201.

When the analysis unit 61 receives the measurement data based on a quality control substance from the measurement unit 50, the analysis unit 61 generates the measurement result group 201 based on the received measurement data. When the analysis unit 61 receives the measurement data based on a specimen from the measurement unit 50, the analysis unit 61 generates the measurement result group 202 based on the received measurement data.

When the analysis unit 61 has generated the measurement result group 201, the analysis unit 61 transmits the generated measurement result group 201 as the first quality control information to the management apparatus 30. At this time, the analysis unit 61 calculates XbarM(i) as current statistical information, based on XbarM(i−1) having been calculated for the immediately preceding time, and a plurality of the measurement result groups 202 between the generated measurement result group 201 and the measurement result group 201 having been generated for the immediately preceding time. XbarM represents a value obtained by calculating a weighted average of the measurement results of the plurality of specimens according to a calculation equation described below. XbarM(i) is calculated for each of the measurement items and the sensitivity items. The analysis unit 61 transmits XbarM(i) calculated for each of the measurement items and the sensitivity items, as the second quality control information, to the management apparatus 30.

Specifically, a process performed by the analysis unit 61 that has generated the measurement result group 201 located at the right end in FIG. 5 will be described as an example. As described below, the quality control technique using measurement results from specimens according to the embodiment is based on the Average of Normals method.

The analysis unit 61 selects N measurement result groups 202 from among the measurement result groups 202 between the measurement result group 201 located at the right end, and the immediately preceding measurement result group 201. Specifically, the analysis unit 61 selects the measurement result groups 202 in which the measurement results of the measurement items for the measurement result groups 202 indicate normal values. The measurement result groups 202 in which the measurement results indicate normal values may not necessarily be selected. Any measurement result group 202 that includes a measurement result appropriate for the statistical processing may be selected. In the embodiment, N represents 20. However, N may represent a value other than 20.

A collection of the N measurement result groups 202 having been selected is referred to as "i-th batch". Each of the measurement result groups 202 included in the i-th batch includes measurement results of a plurality of measurement items and measurement results of a plurality of sensitivity items. Hereinafter, one item among the measurement items and the sensitivity items is referred to as "subject item", and a procedure for calculating XbarM(i) for the subject item will be described.

When the measurement result, of the subject item, included in the j-th measurement result group 202 in the i-th batch is referred to as Xbar (j, i), and the statistical information of the (i−1)-th batch for the subject item is referred to as XbarM(i−1), XbarM(i) that represents the statistical information for the subject item in the i-th batch is calculated according to equation (1) shown in FIG. 6. In equation (1) shown in FIG. 6, the value of F is calculated according to equation (2) shown in FIG. 6. The analysis unit 61 performs the above-described procedure for the other items in the i-th batch, and transmits XbarM calculated for each of the measurement items and the sensitivity items, as the second quality control information, to the management apparatus 30.

One batch may be set between two quality control substance measurements, or a plurality of batches may be set therebetween. When the analysis unit 61 has generated the measurement result group 201 located at the right end, the analysis unit 61 may transmit the immediately preceding measurement result group 201, as the first quality control information, to the management apparatus 30, and may transmit XbarM(i) based on the i-th batch, as the second quality control information, to the management apparatus 30. That is, XbarM in a period that immediately precedes generation of the first quality control information may be transmitted or XbarM in a period that immediately follows the generation may be transmitted.

Figure 7:
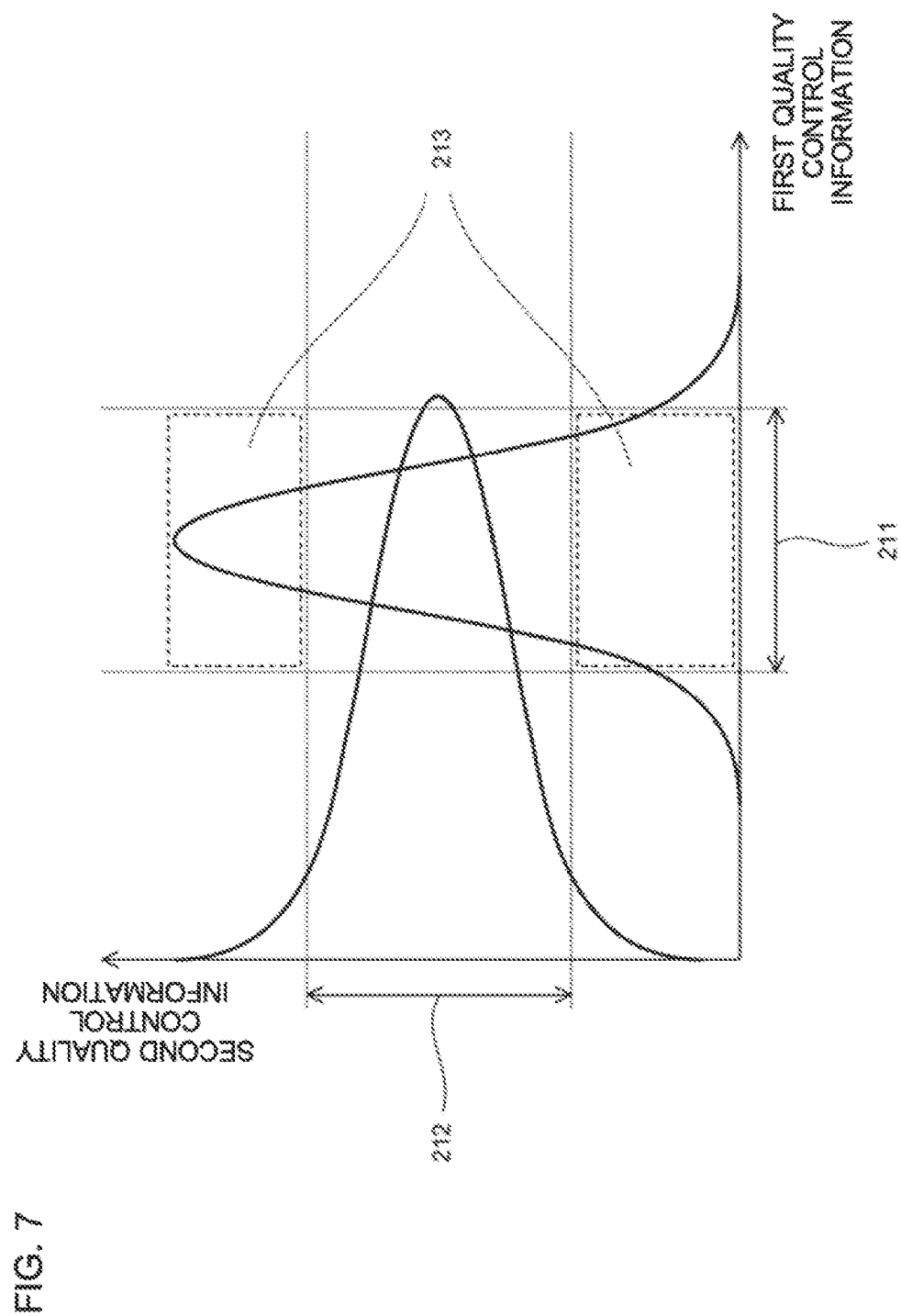
FIG. 7 illustrates characteristics of first quality control information and second quality control information according to the embodiment.

FIG. 7 shows a graph in which a combination of the first quality control information and the second quality control information, for a predetermined item, generated at the same timing is plotted in a coordinate space in which two axes represent the first quality control information and the second quality control information. In the graph, a histogram representing frequencies for the first quality control information and the second quality control information is also shown. The horizontal axis represents values of the first quality control information. On the horizontal axis, a range 211, in which the quality control is determined as being appropriate when determination as to the quality control is performed based on the first quality control information, is indicated. The vertical axis represents values of the second quality control information. On the vertical axis, a range 212, in which the quality control is determined as being appropriate when determination as to the quality control is performed based on the second quality control information, is indicated.

In general, determination as to the quality control is performed based on only the first quality control information obtained from a quality control substance. In this case, for example, when coordinate points are included in the range 211, the quality control of the analyzer 20 is determined as being appropriate. When coordinate points are outside the range 211, the quality control of the analyzer 20 is determined as being not appropriate. Meanwhile, for example, in a case where determination as to the quality control is performed based on the second quality control information obtained from a plurality of specimens, the quality control of the analyzer 20 is determined as being appropriate when coordinate points are included in the range 212, and the quality control of the analyzer 20 is determined as being not appropriate when coordinate points are outside the range 212.

Therefore, if the second quality control information in addition to the first quality control information is used for determination as to the quality control, when coordinate points are included in regions 213 indicated by broken lines in FIG. 7, the quality control is determined as being not appropriate based on the second quality control information although the quality control is determined as being appropriate based on the first quality control information. That is, when the second quality control information in addition to the first quality control information is used for determination as to the quality control, abnormality in quality control which cannot be detected by determination based on only the first quality control information can be detected.

Next, characteristics of the first quality control information and the second quality control information will be described.

Figure 8B:
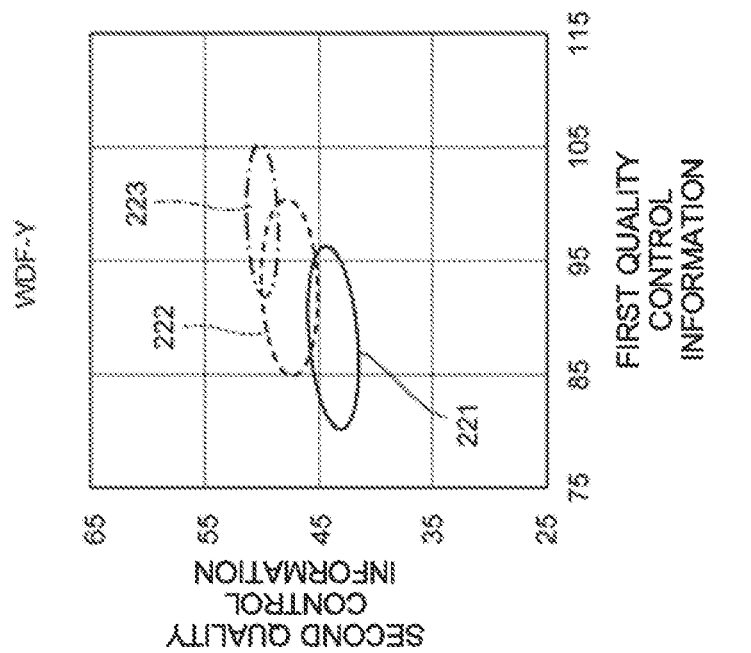
FIG. 8B shows a graph in which difference in a state of quality control between analyzers can be recognized based on the second quality control information according to the embodiment.
Figure 8A:
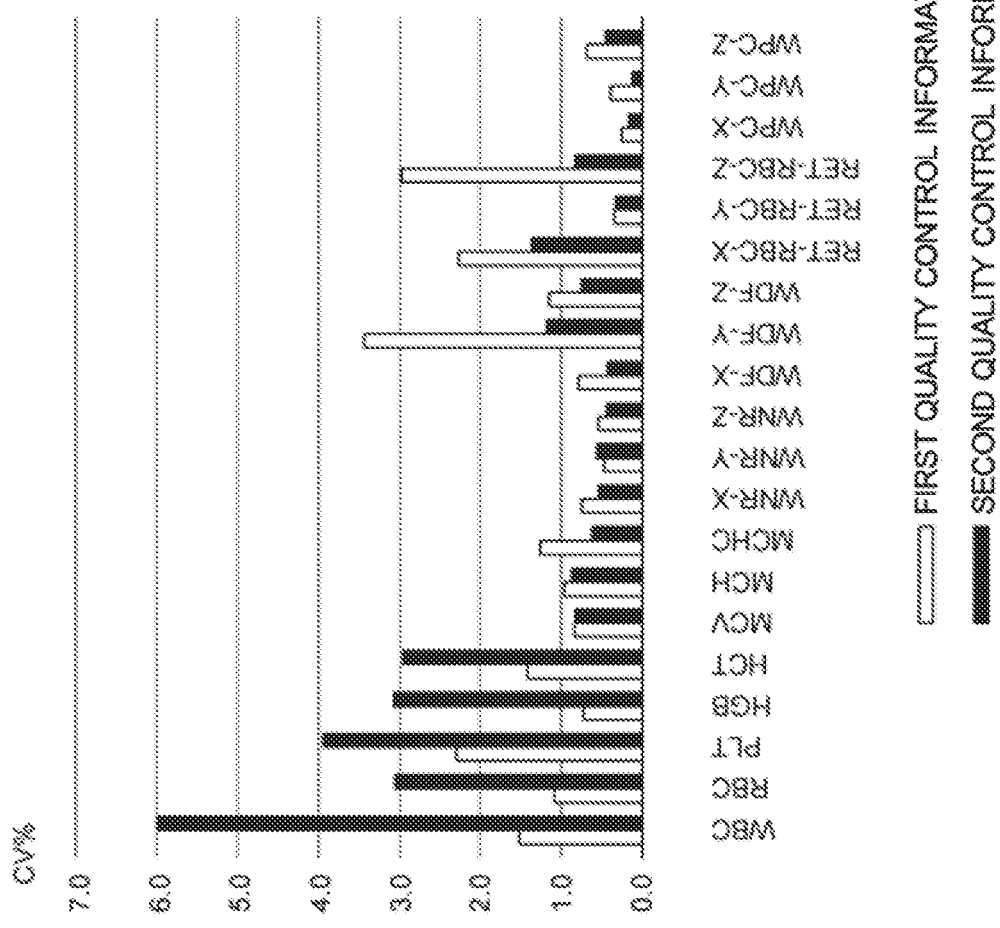
FIG. 8A shows a graph for comparing coefficients of variations of the first quality control information and the second quality control information according to the embodiment.

FIG. 8A illustrates, for each item, a coefficient of variation CV of the quality control information which is actually obtained from eighteen analyzers 20 which are installed in six facilities 12. WBC represents the number of white blood cells. RBC represents the number of red blood cells. PLT represents the number of platelets. HGB represents an amount of hemoglobin. HCT represents a hematocrit value. MCV represents a mean corpuscular volume. MCH represents a mean corpuscular hemoglobin. MCHC represents a mean corpuscular hemoglobin concentration.

WNR-X, WNR-Y, and WNR-Z represent measurement results based on the WNR measurement sample, and represent a side scattered light intensity, a fluorescence intensity, and a forward scattered light intensity, respectively. WDF-X, WDF-Y, and WDF-Z represent measurement results based on the WDF measurement sample, and represent a side scattered light intensity, a fluorescence intensity, and a forward scattered light intensity, respectively. RET-RBC-X, RET-RBC-Y, and RET-RBC-Z represent measurement results based on the RET measurement sample, and represent a side scattered light intensity, a fluorescence intensity, and a forward scattered light intensity, respectively. WPC-X, WPC-Y, and WPC-Z represent measurement results based on the WPC measurement sample, and represent a side scattered light intensity, a fluorescence intensity, and a forward scattered light intensity, respectively. The quality control substances with the same lot number are used in each analyzer 20. N for calculation of the second quality control information is 20.

As shown in FIG. 8A, for the measurement items from WBC to MCHC, that is, the CBC items, the coefficient of variation CV of the first quality control information is generally less than the coefficient of variation CV of the second quality control information. In particular, for the measurement items from WBC to HCT, the coefficient of variation CV of the first quality control information is substantially less than the coefficient of variation CV of the second quality control information.

Therefore, it can be understood that, when the quality control based on the CBC items is performed, the first quality control information obtained by measuring the quality control substance is preferably used. Conventionally, the first quality control information of the CBC items is obtained, and, in addition thereto, the second quality control information of the CBC items is also obtained. However, as described above, variation of the second quality control information of the CBC items is great. Therefore, the first quality control information has been preferentially used for the quality control based on the CBC items.

Meanwhile, for the sensitivity items from WNR-X to WPC-Z, the coefficient of variation CV of the second quality control information is generally less than the coefficient of variation CV of the first quality control information. In particular, for some of the sensitivity items based on the WDF measurement sample and the RET measurement sample, the coefficient of variation CV of the second quality control information is substantially less than the coefficient of variation CV of the first quality control information. Therefore, it can be understood that, when the quality control based on the sensitivity items is performed, the second quality control information obtained by measuring a plurality of specimens is preferably used.

Thus, the present inventors have found that comparison between the coefficient of variation CV of the first quality control information and the coefficient of variation CV of the second quality control information for each of the measurement items and the sensitivity items indicates that the coefficient of variation CV of the second quality control information is less for the sensitivity items. Therefore, when the first quality control information is used for the measurement items and the second quality control information is used for the sensitivity items in the quality control, variation of the quality control information can be reduced, and occurrence of abnormality in quality control can be thus accurately recognized, thereby stabilizing the quality control.

As described above, the value of the coefficient of variation CV of the first quality control information is less for the measurement items, and the value of the coefficient of variation CV of the second quality control information is less for the sensitivity items. Therefore, as shown in FIG. 7, when the first quality control information and the second quality control information are used in combination to determine whether or not abnormality in quality control may have occurred, the measurement results of the measurement items in the first quality control information are preferably used, and the measurement results of the sensitivity items in the second quality control information are preferably used. In this case, when coordinate points based on the first quality control information and the second quality control information are included in both of the ranges 211 and 212 shown in FIG. 7, it is determined that the quality control is appropriately performed. Otherwise, it is determined that abnormality has occurred in the quality control.

For example, in a case where the analyzer 20 does not transmit the first quality control information and the second quality control information to the management apparatus 30, and the quality control is performed in the facility 12 in which the analyzer 20 is installed, determination as to abnormality in quality control is performed by using all the items of the first quality control information and the second quality control information. In such a quality control, as shown in FIG. 8A, since each of variations of the first quality control information and the second quality control information is great for some items, reporting as to abnormality in quality control which is determined based on items, for which the variation is great, among the items of the first quality control information and the second quality control information, may be frequently performed with low reliability. If such reporting with low reliability is frequently performed, an operator who views the report information is unlikely to rely on the report information.

However, the quality control system 10 of the embodiment is configured to perform reporting as to abnormality in quality control with high reliability based on items, for which the variation is small, among the items of the first quality control information and the second quality control information. Specifically, determination as to abnormality in quality control is performed by using the first quality control information for the measurement items, and determination as to abnormality in quality control is performed by using the second quality control information for the sensitivity items. Thus, only abnormality in quality control determined with high reliability is reported. When an operator is thus provided with only report information with high reliability, the operator is allowed to appropriately evaluate the state of the quality control of the analyzer 20, and take measures necessary for improving the quality control.

The investigation by the present inventors indicates that the coefficient of variation CV of the second quality control information can be reduced also for the measurement items when the value of N in calculation of the second quality control information is further increased, e.g., N is set to 99. Accordingly, by the value of N being increased, the quality control may be stabilized also when the second quality control information is used in the quality control based on the measurement items.

FIG. 8B shows a graph in which a combination of the first quality control information and the second quality control information generated at the same timing is plotted in a coordinate space in which two axes represent the first quality control information and the second quality control information. Regions 221, 222, and 223 illustrate regions in which coordinate points, each representing a combination of the first quality control information and the second quality control information, which are obtained from three different analyzers 20, are distributed for the item of WDF-Y.

As shown in FIG. 8B, in each of the regions 221 to 223, the width, in the longitudinal direction, corresponding to the second quality control information is less than the width, in the transverse direction, corresponding to the first quality control information. This indicates that the coefficient of variation CV of the second quality control information is less than the coefficient of variation CV of the first quality control information for the item of WDF-Y shown in FIG. 8A.

As to the first quality control information represented by the horizontal axis, the regions 221 to 223 overlap each other. Thus, it can be said that the first quality control information do not greatly vary among the analyzers 20. Meanwhile, as to the second quality control information represented by the vertical axis, although the adjacent regions overlap each other, the regions 221 and 223 do not overlap each other. Therefore, it can be said that the second quality control information varies among the analyzers 20. Accordingly, when the second quality control information is used for the sensitivity items, a degree of deviation of the quality control of the target analyzer 20 from the quality control of the other analyzers 20 can be recognized. In other words, when a distribution of the second quality control information is obtained for the sensitivity items for each analyzer 20, difference in a state of the quality control between the analyzer 20 for which the quality control is performed and the other analyzers 20 can be recognized.

Figure 9:
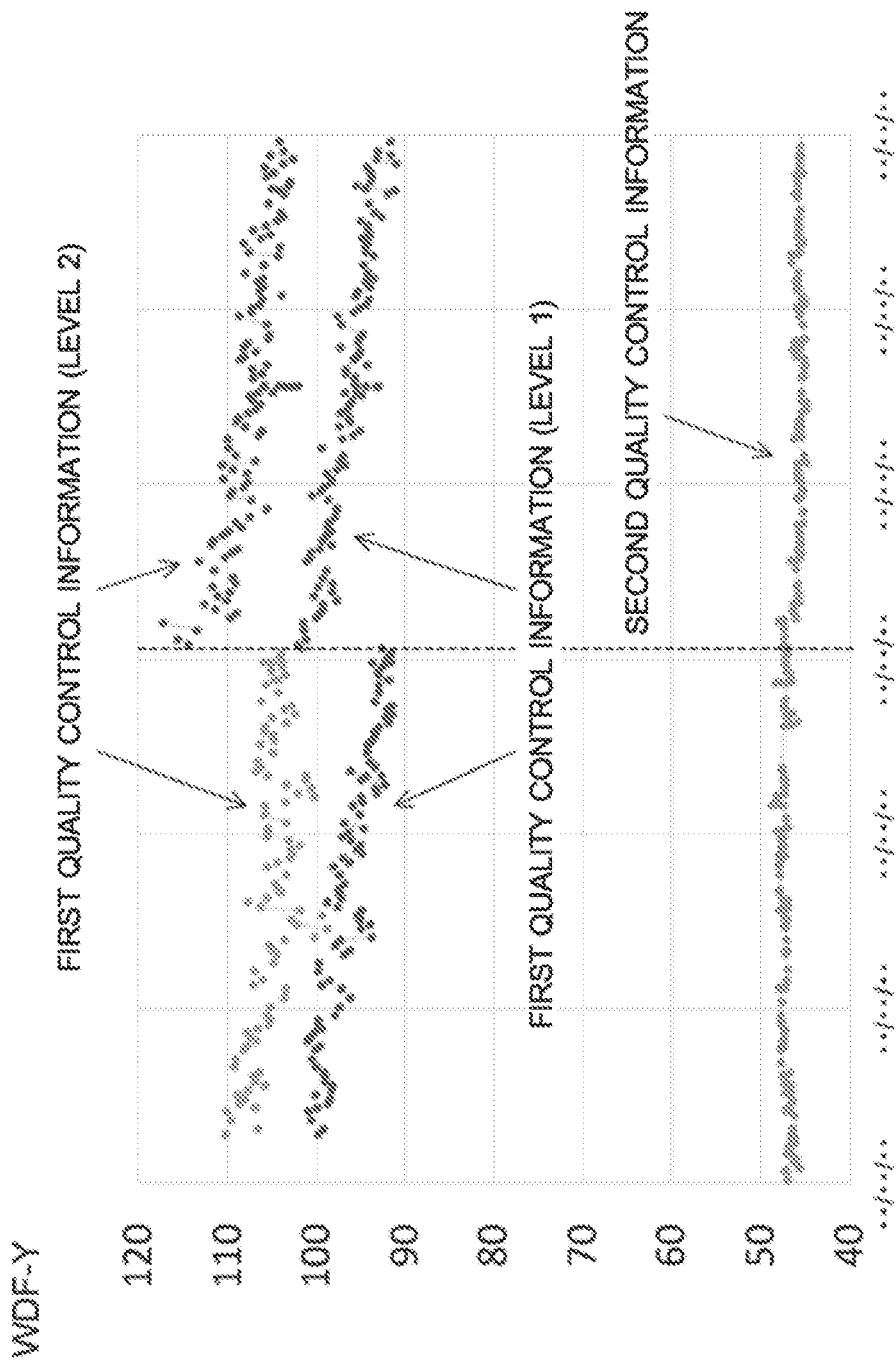
FIG. 9 shows a graph chronologically indicating a first quality control substance and a second quality control substance having been obtained, according to the embodiment.

In a graph shown in FIG. 9, the horizontal axis chronologically represents dates, and the vertical axis represents values of the quality control information for WDF-Y. In the actual quality control, as shown in FIG. 9, two kinds of quality control substances having different concentration levels are measured, and the first quality control information is calculated for each concentration level. The broken line indicated near the center of the graph in FIG. 9 represents a time at which the quality control substance is changed.

As shown in FIG. 9, the value of the first quality control information obtained by measuring the quality control substance tends to be reduced with elapse of time. The value of the first quality control information tends to greatly change when the quality control substance is changed. Meanwhile, the second quality control information obtained by measuring a plurality of specimens is almost constant even if time elapses. This also indicates that a degree of variation of the second quality control information is less than that of the first quality control information for the sensitivity items. Accordingly, when the second quality control information is used, the value of the quality control information is unlikely to vary, thereby stabilizing the quality control.

The quality control substance is artificially generated, and is generally stored in a certain usage period of time and used for the quality control, so that the quality control substance may be deteriorated over time in the usage period of time. Meanwhile, a fresh specimen is measured in order to assure accuracy of analysis. Reactivity of a dye from which fluorescence is generated is different according to a deterioration state of a sample to be dyed. Therefore, variation in reactivity of a specimen to a dye is less than variation in reactivity of the quality control substance to the dye. For these reasons, as shown in FIG. 9, the first quality control information changes with elapse of time, and the second quality control information is almost constant regardless of elapse of time. Thus, when fluorescence is used as light intensity for obtaining the first quality control information and the second quality control information, variation of the second quality control information can be substantially reduced as compared to variation of the first quality control information. Therefore, the state of the quality control can be appropriately evaluated by outputting the second quality control information.

Next, the process performed by the quality control system 10 will be described with reference to FIG. 10 to FIG. 12.

Figure 10:
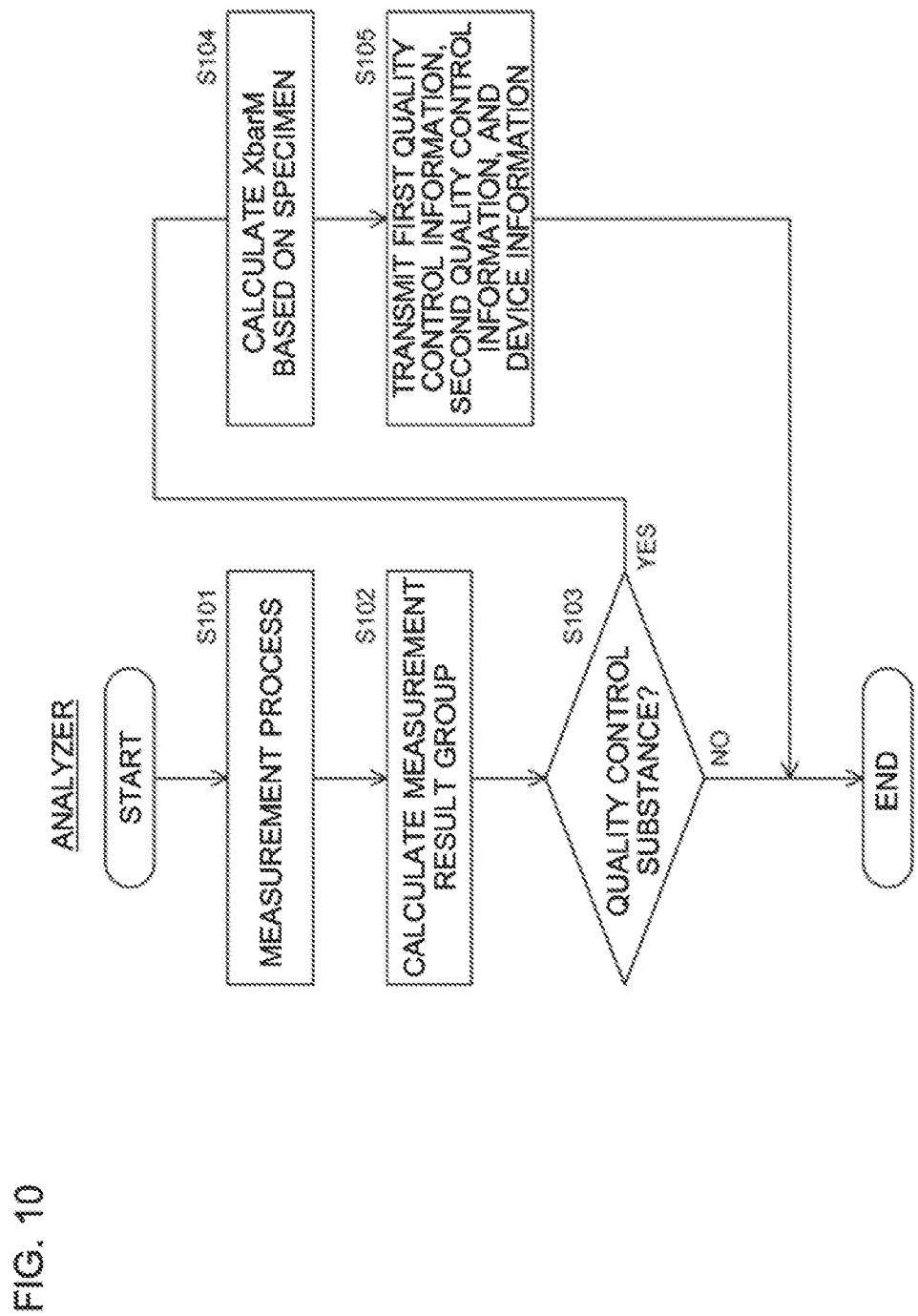
FIG. 10 is a flow chart showing a process performed by the analyzer according to the embodiment.

FIG. 10 is a flow chart showing a process performed by the analyzer 20. Each step in FIG. 10 is performed by the measurement controller 51 of the measurement unit 50 or the analysis unit 61 of the information processing unit 60.

When the analysis unit 61 transmits an instruction for starting measurement to the measurement unit 50, the measurement controller 51 controls each component of the measurement unit 50 to measure a quality control substance or a specimen in step S101. As described above, the measurement controller 51 transmits the measurement data obtained by the measurement, to the information processing unit 60.

In step S102, the analysis unit 61 calculates a measurement result group based on the received measurement data, and stores the calculated measurement result group in the storage unit 62. Specifically, when the quality control substance is measured in step S101, the analysis unit 61 calculates the measurement result group 201 shown in FIG. 5 based on the received measurement data. When a specimen is measured in step S101, the analysis unit 61 calculates the measurement result group 202 shown in FIG. 5 based on the received measurement data. The calculated measurement result group 201 or measurement result group 202 include measurement results of the measurement items and the sensitivity items as described above.

In step S103, the analysis unit 61 determines whether or not the quality control substance has been measured in the most recent step S101. When the quality control substance has not been measured in the most recent step S101, that is, when the specimen has been measured in the most recent step S101, the process is ended. When the quality control substance has been measured in the most recent step S101, the analysis unit 61 calculates, in step S104, the current XbarM(i) based on the measurement result groups 202 in the i-th batch and XbarM(i−1) having been calculated for the immediately preceding time, for each of the measurement items and the sensitivity items, according to the procedure described with reference to FIGS. 5 and 6.

Subsequently, in step S105, the analysis unit 61 transmits the first quality control information, the second quality control information, and the device information to the management apparatus 30. The first quality control information is the measurement result group 201 that includes the measurement results, for each of the measurement items and the sensitivity items, obtained by measuring the quality control substance. The second quality control information represents XbarM(i), for each of the measurement items and the sensitivity items, calculated in step S104.

In the process shown in FIG. 10, each piece of the information in step S105 is transmitted to the management apparatus 30 when the quality control substance is measured. However, the embodiment is not limited thereto. The information in step S105 may be transmitted to the management apparatus 30 at a predetermined time, for example, at six hour intervals.

Figure 11:
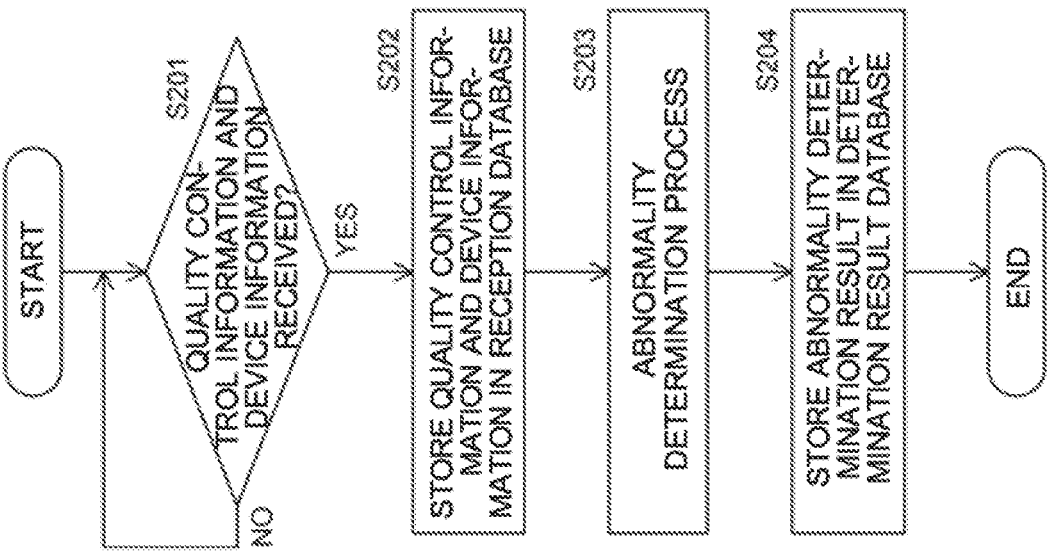
FIG. 11 is a flow chart showing a process performed by the management apparatus according to the embodiment.

FIG. 11 is a flow chart showing a process performed by the management apparatus 30.

In step S201, the controller 31 of the management apparatus 30 determines whether or not the first quality control information, the second quality control information, and the device information have been received. When the information transmitted in the process step of step S105 in FIG. 10 has been received, the controller 31 operates, in step S202, to store the first quality control information, the second quality control information, and the device information which have been received, in the reception database 32b, such that the first quality control information, the second quality control information, and the device information are associated with each other.

Subsequently, in step S203, the controller 31 performs an abnormality determination process for quality control, based on the information stored in the immediately preceding step S202. The controller 31 determines whether or not the first quality control information, the second quality control information, and the device information which have been received satisfy a predetermined condition, to perform abnormality determination for quality control. The predetermined condition used in the determination of step S203 may be stored in the storage unit 32 of the management apparatus 30 in advance, or may be set by the controller 31 based on the first quality control information, the second quality control information, and the device information which have been obtained from a plurality of the analyzers 20. By the condition being set by the controller 31, a condition based on the characteristics of the analyzer 20 can be set. A specific example of the abnormality determination process will be described below with reference to FIG. 14A to FIG. 15. Subsequently, in step S204, the controller 31 stores, in the determination result database 32c, a result of the abnormality determination process performed in step S203.

Figure 12:
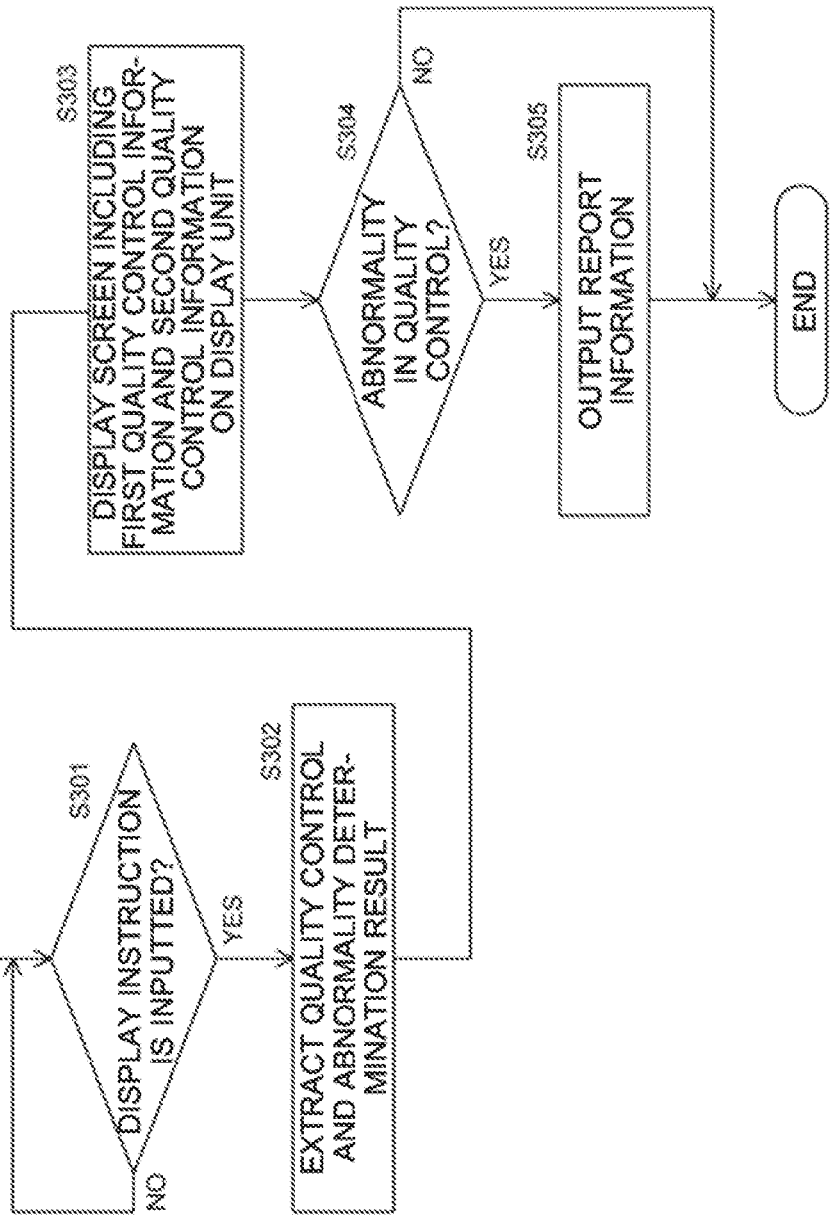
FIG. 12 is a flow chart showing a process performed by the management apparatus according to the embodiment.

FIG. 12 is a flow chart showing a process performed by the management apparatus 30.

In step S301, the controller 31 of the management apparatus 30 determines whether or not a display instruction from a staff member in charge of the monitor has been inputted through the input unit 33. The display instruction includes a facility number, an analyzer number, a display time, a name of an item, and the like. When the display instruction has been inputted, the controller 31 extracts, in step S302, the first quality control information, the second quality control information, and an abnormality determination result, from the reception database 32b and the determination result database 32c, based on the facility number, the analyzer number, the display time, the name of the item, and the like which are included in the display request.

Subsequently, in step S303, the controller 31 causes the display unit 40 to display a screen including the first quality control information and the second quality control information. The controller 31 may cause the display unit 40 to separately display a screen on which the first quality control information can be referred to, and a screen on which the second quality control information can be referred to, according to switching of a tab. In step S304, the controller 31 determines whether or not the abnormality determination result having been extracted in step S302 indicates "abnormality in quality control". When the abnormality determination result indicates "abnormality in quality control", the controller 31 operates, in step S305, so as to output report information indicating that abnormality in quality control has occurred in the target analyzer 20. Specifically, the controller 31 operates to indicate that abnormality in quality control has occurred, on the screen displayed on the display unit 40 in step S303.

In step S305, the controller 31 may operate so as to output sound indicating that abnormality in quality control has occurred, from a speaker of the management apparatus 30 or another device, or may operate so as to output the information as, for example, vibration which can be recognized by a staff member in charge of the monitor, from a vibration generation device of the management apparatus 30 or another device. The report information may include information that indicates a determination condition, of abnormality in quality control, having been satisfied.

In the process shown in FIG. 12, the screen including the quality control information and the like is displayed on the display unit 40 according to the display instruction being inputted by a staff member in charge of the monitor. However, at a time when the quality control information and the like are stored in the reception database 32b, and the abnormality determination result is stored in the determination result database 32c in FIG. 11, the screen including the quality control information and the like may be automatically displayed on the display unit 40.

In the process shown in FIG. 11, the abnormality determination process and storing of the abnormality determination result are performed at a time when the management apparatus 30 receives the quality control information and the like from the analyzer 20. However, the embodiment is not limited thereto. The abnormality determination process and storing of the abnormality determination result may be performed when a display instruction is inputted in step S301 in FIG. 12.

In the process shown in FIG. 12, also when a display request is received from an apparatus other than the management apparatus 30, for example, from another device in the facility 11, the controller 31 may transmit the quality control information and the abnormality determination result to the device that has transmitted the display request. In this case, the quality control information and the abnormality determination result are displayed by the device that has transmitted the display request.

As described above, when the screen on which the first quality control information and the second quality control information can be referred to is displayed on the display unit 40 in step S303, the staff member in charge of the monitor is allowed to visually know the state of the quality control of the analyzer 20. When the report information indicating that abnormality in quality control has occurred in the analyzer 20 is outputted in step S305, the staff member in charge of the monitor is allowed to know that abnormality in quality control has occurred in the analyzer 20. Thus, the staff member in charge of the monitor is allowed to take measures for improving the quality control by, for example, making contact with the laboratory technician in the facility 12 that has the analyzer 20 in which abnormality in quality control has occurred.

Figure 13A:
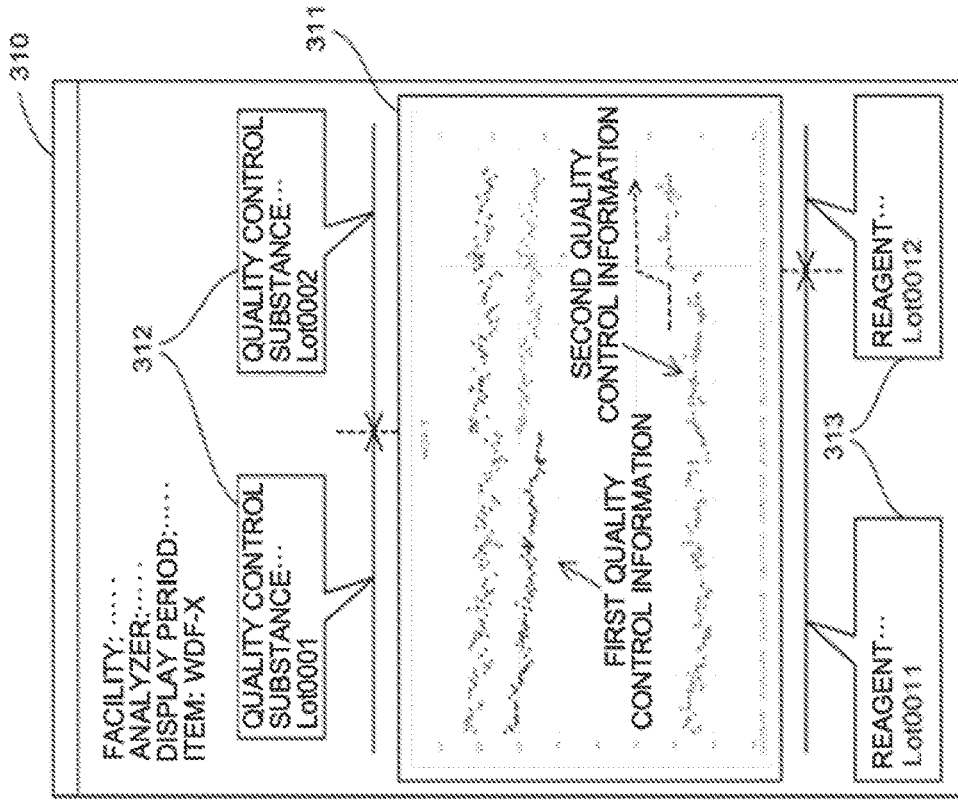
FIG. 13A illustrates an example of a screen displayed on a display unit according to the embodiment.

FIGS. 13A, B illustrate examples of screens displayed in step S303 in FIG. 12.

Figure 13B:
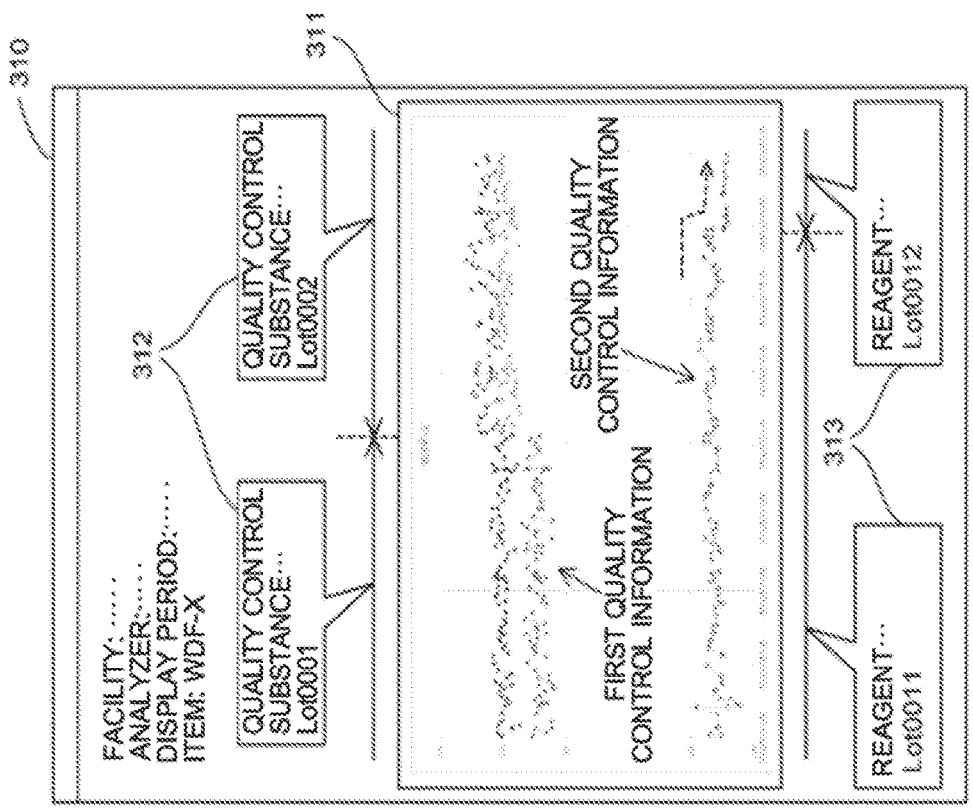
FIG. 13B illustrates an example of a screen displayed on the display unit according to the embodiment.

A screen 310 shown in FIG. 13A, B includes a graph 311 chronologically indicating the first quality control information and the second quality control information; a display region 312 indicating a name and a lot number of a quality control substance; and a display region 313 indicating a name and a lot number of a reagent. The screen 310 shown in FIG. 13A represents a state where WDF-X is displayed as the item. The screen 310 shown in FIG. 13B represents a state where WDF-Y is displayed as the item.

The staff member, in charge of the monitor, who operates the management apparatus 30 is allowed to confirm a state in which the first quality control information and the second quality control information chronologically change, by referring to the screen 310. The staff member in charge of the monitor is allowed to know, by referring to the screen 310, a time at which the first quality control information and the second quality control information greatly change, and that abnormality may have occurred in the quality control at the time. Therefore, at the time, the staff member in charge of the monitor is allowed to estimate abnormality in quality control and the cause thereof by checking how the quality control information has changed, and by further recognizing other information to be examined for the quality control as appropriate, thereby appropriately performing the quality control. Moreover, the staff member in charge of the monitor is allowed to compare the change of the first quality control information and the change of the second quality control information, on one screen 310. Accordingly, the staff member in charge of the monitor compares the two kinds of the quality control information, to smoothly and simply determine whether or not abnormality may have occurred in quality control.

The example of the screen 310 shown in FIG. 13A, B indicates that the second quality control information changes at a time when a reagent lot is changed. That is, in the case shown in FIG. 13A, the value of the second quality control information for WDF-X is slightly decreased as indicated by a broken line arrow in the graph 311 at a time when the reagent lot is changed. In the case shown in FIG. 13B, the value of the second quality control information for WDF-Y is slightly increased as indicated by a broken line arrow in the graph 311 at a time when the reagent lot is changed. However, in each of the cases shown in FIGS. 13A, B, the first quality control information does not particularly change. In a case where the second quality control information based on the specimen changes although the first quality control information based on the quality control substance does not change, a staff member, in charge of the monitor, who views the screen 310 is allowed to infer that a problem may have arisen in the reagent.

When, as shown in FIGS. 13A, B, the first quality control information is normal, and the second quality control information greatly changes and satisfies a predetermined condition, report information indicating that abnormality may have occurred in the reagent may be outputted. In this case, for example, "abnormality in reagent" may be displayed on the screen 310 in FIG. 13A, B, or sound or vibration for reporting abnormality in reagent may be outputted. Thus, the staff member in charge of the monitor is allowed to know that abnormality may have occurred in the reagent.

Figure 14A:
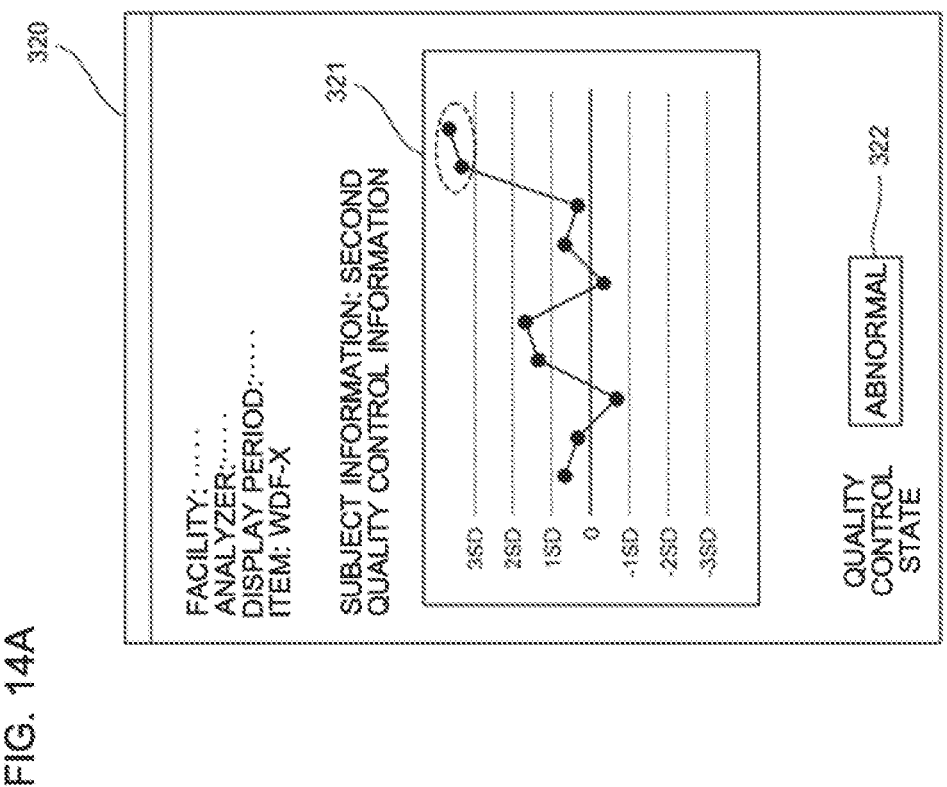
FIG. 14A illustrates an example of a screen displayed on the display unit according to the embodiment.

FIG. 14A illustrates an example of a screen displayed in step S305 in FIG. 12.

A screen 320 shown in FIG. 14A includes a graph 321 that chronologically indicates the quality control information, and a display region 322 indicating a quality control state. The screen 320 shown in FIG. 14A indicates a state where WDF-Y is displayed as the item, and a state where the second quality control information is displayed as the quality control information to be referred to. In the example shown in FIG. 14A, since the most recently obtained values continuously indicate values outside a predetermined variation range, it is determined in step S203 in FIG. 11 that abnormality in quality control has occurred. More specifically, since two values that were most recently obtained are above 3SD, it is determined that abnormality in quality control has occurred. SD represents Standard Deviation. When such a condition is used, it can be appropriately determined that abnormality in quality control may have occurred in the analyzer 20. When it is determined that abnormality in quality control has occurred, "abnormality has occurred" is displayed in the display region 322.

Figure 14B:
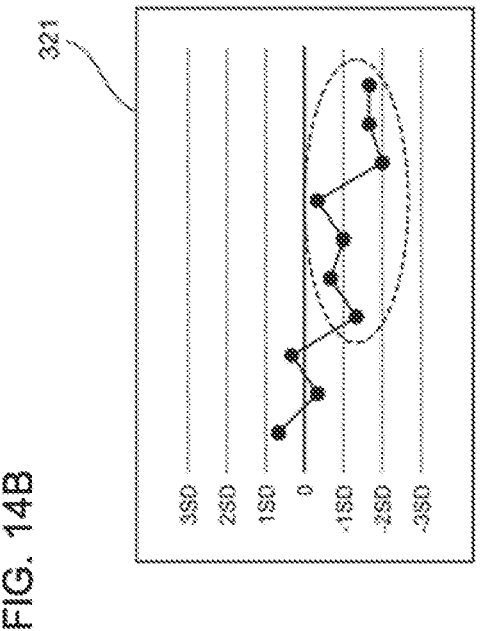
FIG. 14B shows a graph for illustrating quality control abnormality determination according to modification.
Figure 14C:
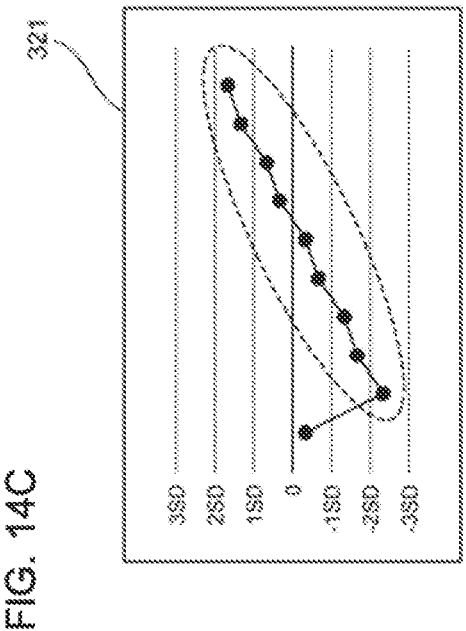
FIG. 14C shows a graph for illustrating quality control abnormality determination according to modification.

When one value that was most recently obtained is outside a predetermined variation range, it may be determined that abnormality in quality control has occurred. As shown in FIG. 14B, when the most recently obtained values continuously deviate to the plus side or minus side relative to the center line for a predetermined number of times, it may be determined that abnormality in quality control has occurred. As shown in FIG. 14C, when the most recently obtained points continuously ascend or descend for a predetermined number of times, it may be determined that abnormality in quality control has occurred.

The center line and the variation range indicated in the graph 321 are set based on a plurality of values of the subject item from the target analyzer 20. The center line and the variation range indicated in the graph 321 may be set based on a plurality of values of the subject item from the target analyzer 20 and other analyzers 20. In this case, the quality control information of the target analyzer 20 can be compared with the quality control information of other analyzers 20.

A staff member, in charge of the monitor, who operates the management apparatus 30 is allowed to correctly know, by referring to the screen 320, that the quality control information indicates a value outside a predetermined range in the target analyzer 20, and that abnormality in quality control may have occurred in the target analyzer 20. Thus, the staff member in charge of the monitor is allowed to smoothly check whether or not abnormality in quality control has occurred. The staff member in charge of the monitor is allowed to know the degree of deviation of the quality control of the target analyzer 20 from the quality control of the other analyzers 20. Therefore, the staff member in charge of the monitor is allowed to take measures for adjusting the analyzer 20 to reduce deviation of the quality control.

When the controller 31 of the management apparatus 30 determines whether or not abnormality in quality control has occurred, based on the graph in which two axes represent the first quality control information and the second quality control information as shown in FIG. 7, a screen including a graph as shown in FIG. 7 may be displayed on the display unit 40. In this case, a staff member in charge of the monitor is allowed to smoothly evaluate the quality control by referring to the two kinds of the quality control information. Also when it is determined that abnormality in quality control has occurred, based on the graph as shown in FIG. 7, report information indicating that abnormality in quality control has occurred may be outputted by the management apparatus 30.

Figure 15:
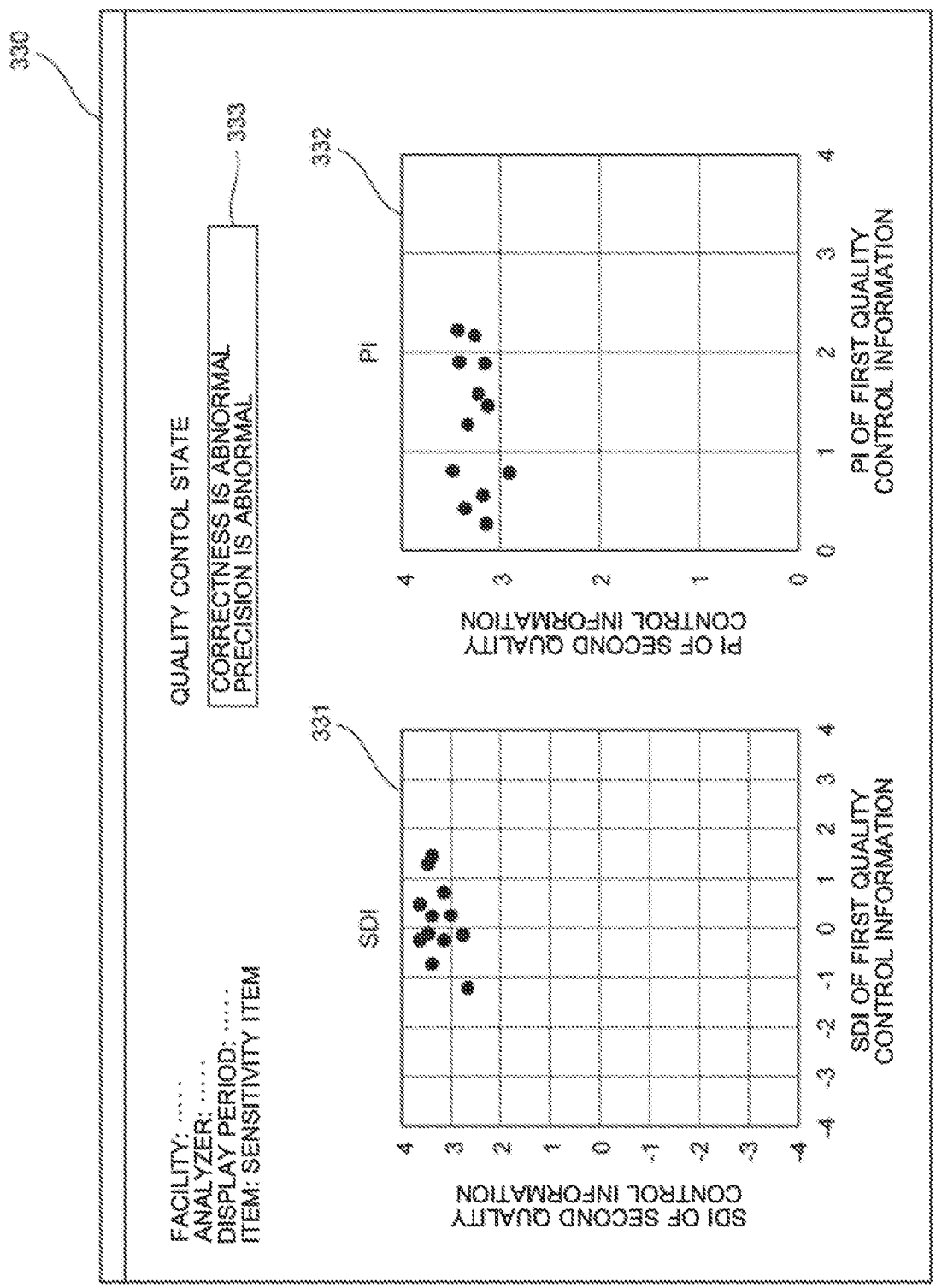
FIG. 15 illustrates an example of a screen displayed on the display unit according to the embodiment.

FIG. 15 illustrates an example of a screen displayed in step S305 in FIG. 12.

A screen 330 shown in FIG. 15 includes graphs 331 and 332, and a display region 333 indicating a quality control state. The graph 331 indicates correctness of the quality control information of the target analyzer 20. That is, the graph 331 represents a degree of approximation of values of the quality control information group to values that are set based on the quality control information obtained from the other analyzers 20. The graph 332 indicates precision of the quality control information of the target analyzer 20. That is, the graph 332 indicates a degree of approximation of the width of variation of the quality control information to a width in a predetermined width range which is set based on the quality control information obtained from the other analyzers 20.

In the graph 331, the horizontal axis and the vertical axis represent SDI, for a subject item, of the first quality control information and SDI, for the subject item, of the second quality control information, respectively. SDI, for a subject item, of the quality control information of the target analyzer 20 is calculated according to the following equation.

$$SDI = (\text{measured value obtained from target analyzer} - \text{average of measured values obtained from analyzers of all the facilities})/\text{the entire SD}$$

In the graph 332, the horizontal axis and the vertical axis represent PI, for a subject item, of the first quality control information and PI, for the subject item, of the second quality control information, respectively. PI, for a subject item, of the quality control information of the target analyzer 20 is calculated according to the following equation.

$$PI = \text{SD of measured values obtained from target analyzer}/\text{average of SDs of measured values obtained from analyzers of all the facilities}$$

In the above-described two equations, the "measured value" represents a measurement result of the subject item for the first quality control information, and represents the statistical information of the subject item for the second quality control information.

For example, a case where one point is plotted in each of the graphs 331 and 332 in measurement in one day, will be described. When the quality control substance is measured twice, i.e., in the morning and evening, SDI and PI of the first quality control information in one plotting are calculated based on two measurement results according to the above-described equations. In this case, the "measured value obtained from target analyzer" in the equation for calculating the SDI is an average value of the two measurement results. In this case, when five batches are set between two measurements of the quality control substance, SDI and PI of the second quality control information in one plotting are calculated based on five pieces of the statistical information according to the above-described equations. In this case, the "measured value obtained from target analyzer" in the equation for calculating SDI is an average value of the five pieces of the statistical information. One point may be plotted in each of the graphs 331 and 332 in, for example, measurement in one week instead of one day.

Instead of one point being plotted in the graph 331, 332 based on measured values obtained in a predetermined period of time such as one day or one week, one point may be plotted at a time when the statistical information for each batch is obtained. For example, when the quality control substance is measured in the morning to obtain the first quality control information, SDI and PI of the second quality control information obtained for a plurality of batches may be associated with SDI and PI of the first quality control information obtained in the morning until the quality control substance is measured next. Thus, on the graph 331, 332, a plurality of points are aligned in the vertical direction according to the number of the batches, and change of the quality control state with elapse of time can be recognized.

On the screen 330 shown in FIG. 15, "sensitivity item" is specified as the item. When the sensitivity item is thus specified, SDIs and PIs corresponding to all the sensitivity items are plotted as indicated in the graphs 331 and 332 in FIG. 15. When one item is specified, SDI and PI corresponding to one item are plotted in the graphs 331 and 332, respectively.

In the example of the screen 330 shown in FIG. 15, the sensitivity item is specified as the item, and both SDIs and PIs of the second quality control information are distributed in a region above three. Therefore, it is indicated in the display region 333 that a problem arises in correctness of the quality control information as compared with the other analyzers 20, based on SDI of the second quality control information. It is indicated in the display region 333 that a problem arises in precision of the quality control information as compared with the other analyzers 20, based on PI of the second quality control information.

Thus, when determination as to abnormality in quality control is performed by comparison with the other analyzers 20, determination accuracy can be enhanced as compared with a case where determination as to abnormality in quality control is performed in the analyzer 20. Thus, reporting with low reliability is inhibited from being frequently performed and only reporting with high reliability can be performed. Therefore, a staff member in charge of the monitor is allowed to assuredly inform the laboratory technician of the analyzer 20 by telephone or the like that measures are to be taken for the analyzer 20.

In the example of the screen 330 shown in FIG. 15, although both SDIs and PIs of the first quality control information are distributed in a region below three, both SDIs and PIs of the second quality control information are distributed in the region above three. In this case, if determination is based on the first quality control information only, the quality control may be determined as being not abnormal. However, when the second quality control information is used as in the embodiment, it can be appropriately determined that abnormality in quality control has occurred.

According to the graphs 331 and 332, a cause of the abnormality in quality control can be determined.

For example, when the plotted points are distributed in the upper right portion, the lower right portion, the upper left portion, or the lower left portion in the graph 331, the quality control is determined as being abnormal based on both the first quality control information and the second quality control information. In this case, for example, both the analyzer 20 and the reagent may be determined as being abnormal. When the plotted points are distributed on the upper center side or the lower center side in the graph 331, the quality control is determined as being normal based on the first quality control information, and the quality control is determined as being abnormal based on the second quality control information. In this case, for example, the specimen or the reagent may be determined as being abnormal. When the plotted points are distributed on the left center side or the right center side in the graph 331, the quality control is determined as being abnormal based on the first quality control information and the quality control is determined as being normal based on the second quality control information. In this case, for example, it may be determined that the quality control substance is deteriorated.

Thus, a staff member, in charge of the monitor, who operates the management apparatus 30 is allowed to specify the cause of the abnormality in quality control in detail according to the combination of the first quality control information and the second quality control information. The determination as to abnormality in quality control and the specifying of the cause of the abnormality in quality control as described above, may be automatically performed by the controller 31 of the management apparatus 30 instead of by the determination and specifying of the cause being performed by a staff member in charge of the monitor. The cause of the abnormality in quality control may be specified based on both the graphs 331 and 332.

A staff member in charge of the monitor is allowed to compare the quality control information of the target analyzer 20 with the quality control information of the other analyzers 20 by referring to the screen 330, so that the staff member is allowed to appropriately and accurately recognize the state of the quality control. A content for reporting abnormality in correctness and precision as described above is displayed in the display region 333. Therefore, the staff member in charge of the monitor is allowed to appropriately determine that abnormality in correctness and precision of a measurement result of the analyzer 20 may have occurred.

The content displayed in the display region 333 is not limited to the content indicated in FIG. 15, and may be a content indicating that the quality control of the target analyzer 20 may be performed in a manner different from the quality control of the other analyzers 20. The determination as to abnormality in quality control based on the graphs 331 and 332 may be performed according to both the first quality control information and the second quality control information. When a part or the entirety of the measurement items is selected as items, determination as to abnormality in quality control based on the graphs 331 and 332 may be performed according to the first quality control information.

Next, an example of a method for more specifically finding a cause of abnormality when a staff member in charge of the monitor suspects abnormality in quality control to occur with reference to the screens 310, 320, and 330, will be described.

The staff member in charge of the monitor operates the management apparatus 30 to transmit an instruction for sharing a screen of the display unit 63 of the information processing unit 60, to the analyzer 20 in which abnormality in quality control is suspected to occur. Thus, communication for sharing the screen between the information processing unit 60 of the target analyzer 20, and the management apparatus 30 is performed, and the screen of the display unit 63 is displayed on the display unit 40 of the management apparatus 30. The staff member in charge of the monitor recognizes in more detail the quality control state by referring to the screen of the information processing unit 60 which is displayed on the display unit 40.

Figure 16A:
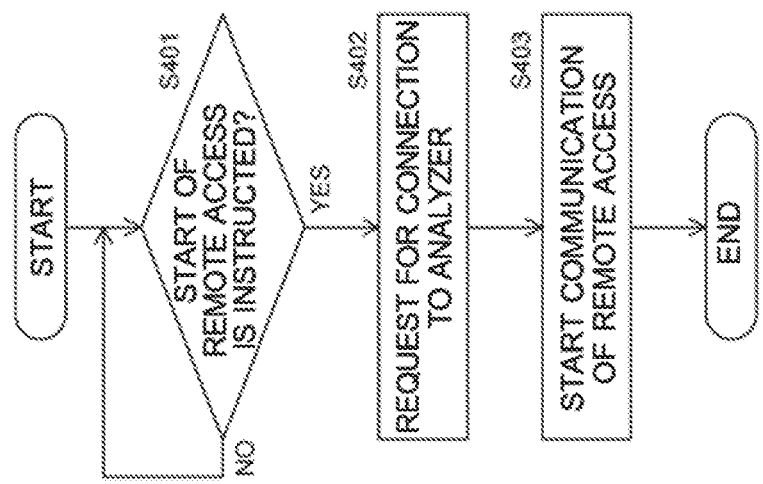
FIG. 16A is a flow chart showing a process performed by the management apparatus according to the embodiment.
Figure 16B:
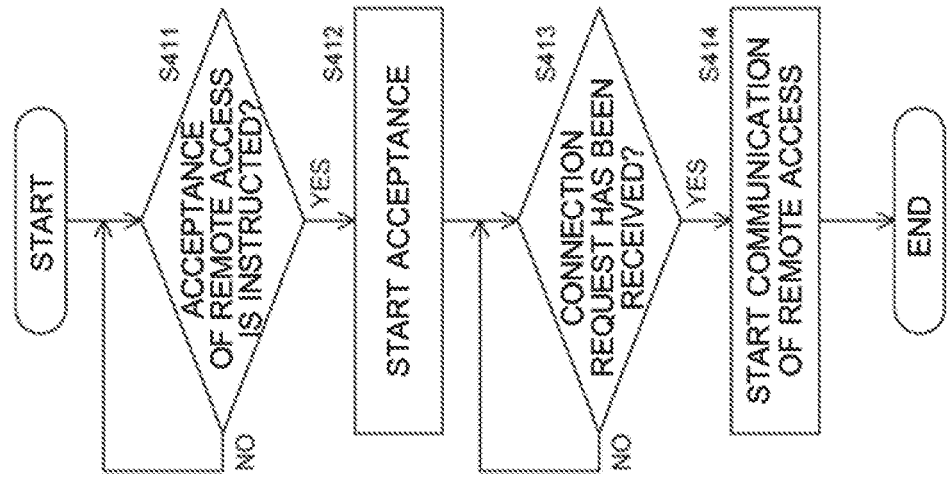
FIG. 16B is a flow chart showing a process performed by the analyzer according to the embodiment.

FIGS. 16A-B are flow charts showing processes performed by the management apparatus 30 and the analyzer 20, respectively.

In the process described below, so-called remote access for performing communication to allow the management apparatus 30 to directly operate the information processing unit 60 is performed in order to share the screen. In the embodiment, for example, the communication application "remote desktop" which can be executed on Microsoft operating system "Windows (registered trademark)" is used as a computer program for performing the remote access.

When determining in step S304 in FIG. 12 that abnormality in quality control has occurred, the controller 31 of the management apparatus 30 starts the process shown in FIG. 16A and causes the display unit 40 to display an input screen for inputting an instruction for starting the remote access. The input screen includes regions in which a user name and a password for logging into the analyzer 20, and an IP address for identifying the analyzer 20 are inputted. The input screen includes a start button for starting the remote access.

As shown in FIG. 16A, in step S401, the controller 31 determines whether or not the instruction for starting the remote access has been inputted through the start button on the input screen. When the instruction for staring the remote access has been inputted, the controller 31 operates, in step S402, to transmit a connection request to the information processing unit 60 of the target analyzer 20 based on the information inputted in the input screen. When communication with the information processing unit 60 of the target analyzer 20 is established, the controller 31 starts communication of the remote access with the information processing unit 60 in step S403.

The process in FIG. 16B is started when the information processing unit 60 of the analyzer 20 is actuated. When a laboratory technician who operates the analyzer 20 is instructed to start the remote access by telephone or the like from the staff member, in charge of the monitor, who operates the management apparatus 30, the laboratory technician operates the input unit 64 to execute a program for starting accepting the remote access.

As shown in FIG. 16B, in step S411, when the program for staring accepting the remote access is executed, the analysis unit 61 of the information processing unit 60 determines whether or not the instruction for accepting the remote access has been inputted. When the instruction for accepting the remote access has been inputted, the analysis unit 61 starts accepting the remote access in step S412. Subsequently, in step S413, the analysis unit 61 determines whether or not the connection request transmitted by the management apparatus 30 in step S402 in FIG. 16A has been received. When the connection request from the management apparatus 30 has been received, the analysis unit 61 starts communication of the remote access with the management apparatus 30 in step S414.

When the management apparatus 30 thus performs the remote access to the analyzer 20, a display screen of the display unit 63 of the information processing unit 60 is displayed on the display unit 40 of the management apparatus 30, and the information processing unit 60 can be operated from the input unit 33 of the management apparatus 30 in a manner similar to a manner in which the information processing unit 60 is operated from the input unit 64 of the information processing unit 60. Thus, the staff member, in charge of the monitor, who operates the management apparatus 30 is allowed to directly operate the information processing unit 60, and, for example, results of measurements, of a specimen and a quality control substance, which are performed by the analysis unit 61 can be displayed on the display unit 40 of the management apparatus 30. Therefore, the staff member in charge of the monitor is allowed to directly confirm the state of the quality control of the analyzer 20 without moving to a place in which the analyzer 20 is installed.

Figure 17A:
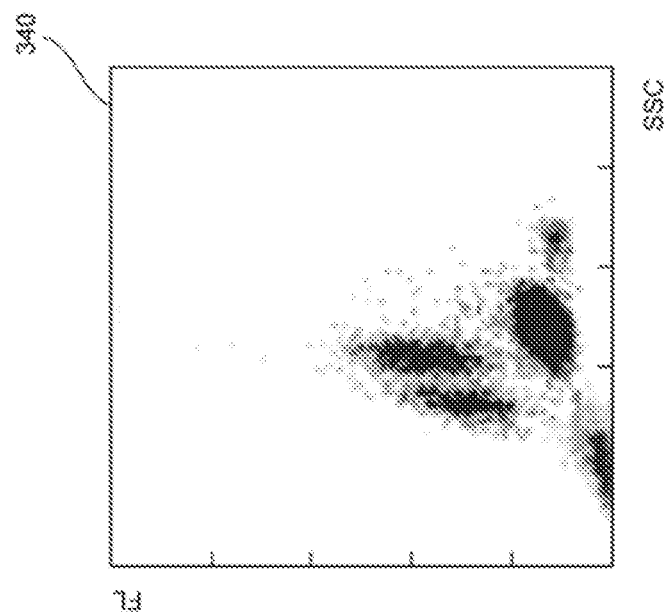
FIG. 17A illustrates an example of a scattergram displayed on the display unit in the case of a genuine reagent being used, according to the embodiment.

Specifically, by the screen being shared, the staff member, in charge of the monitor, who operates the management apparatus 30 is allowed to cause the display unit 40 of the management apparatus 30 to display a scattergram 340 displayed on the display unit 63 of the analyzer 20 as shown in FIG. 17A, B. In the examples shown in FIGS. 17A, B, the horizontal axis of the scattergram 340 represents SSC, that is, the side scattered light intensity, and the vertical axis of the scattergram 340 represents FL, that is, the fluorescence intensity. In the examples shown in FIGS. 17A, B, the scattergram 340 obtained by the WDF measurement sample being measured is indicated, and particles are plotted in the scattergram 340 in which coordinate points represent the side scattered light intensity and the fluorescence intensity obtained by the WDF measurement sample being measured. The particle distribution on the scattergram 340 shown in FIG. 17B is shaped so as to be vertically compressed, that is, to reduce the values of the fluorescence intensity, as compared to the particle distribution on the scattergram 340 shown in FIG. 17A.

Figure 17B:
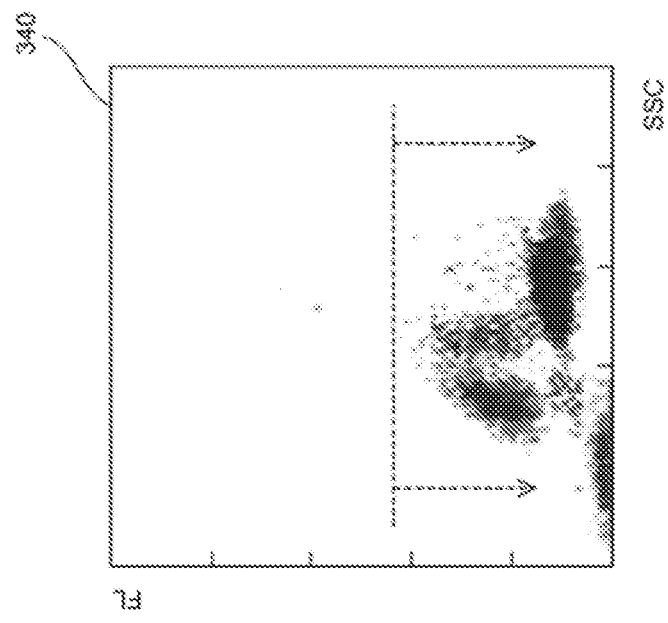
FIG. 17B illustrates an example of a scattergram in the case of a reagent other than a genuine reagent being used, according to the embodiment.
Figure 18:
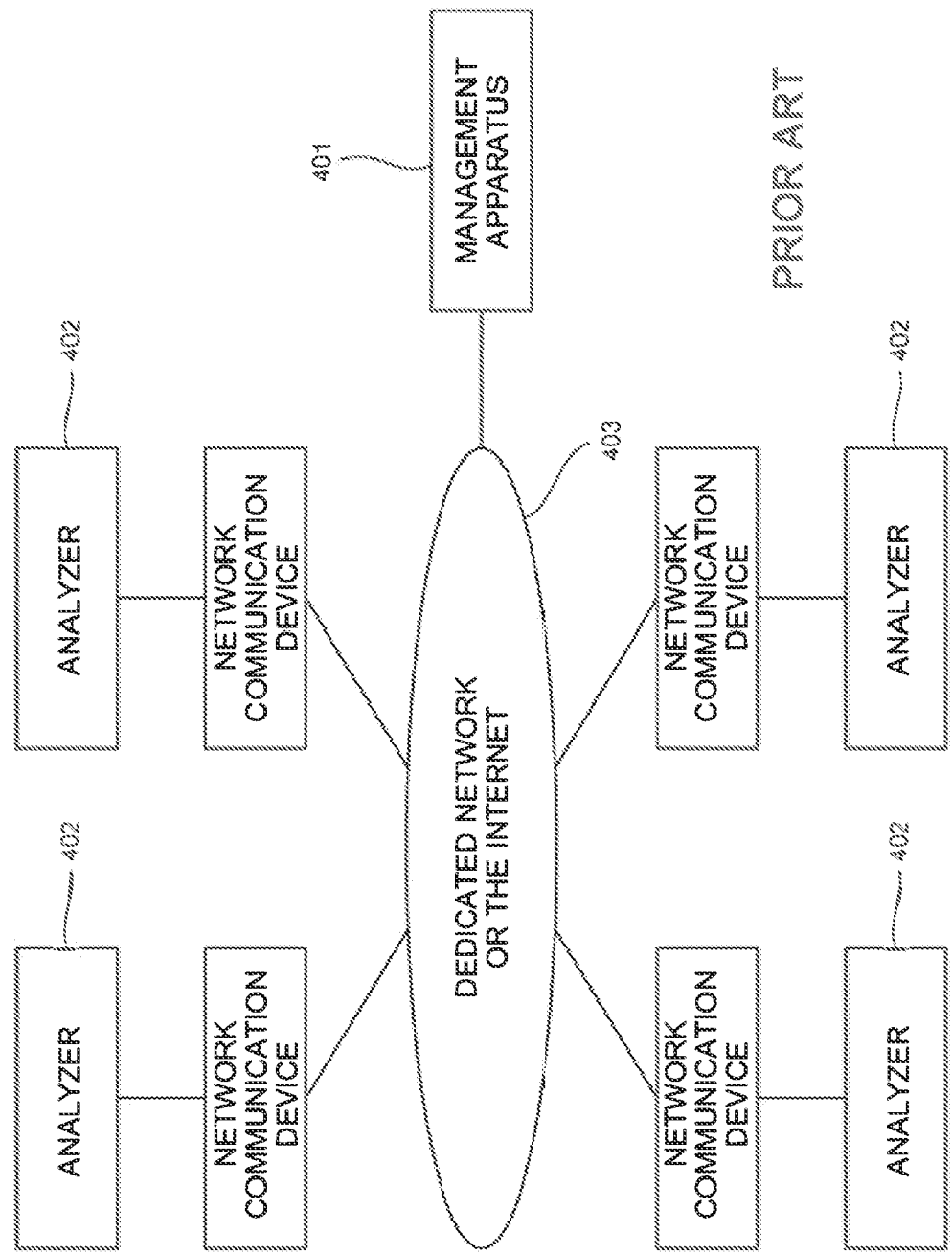
FIG. 18 is a schematic diagram illustrating a structure according to related art.
Figure 19:
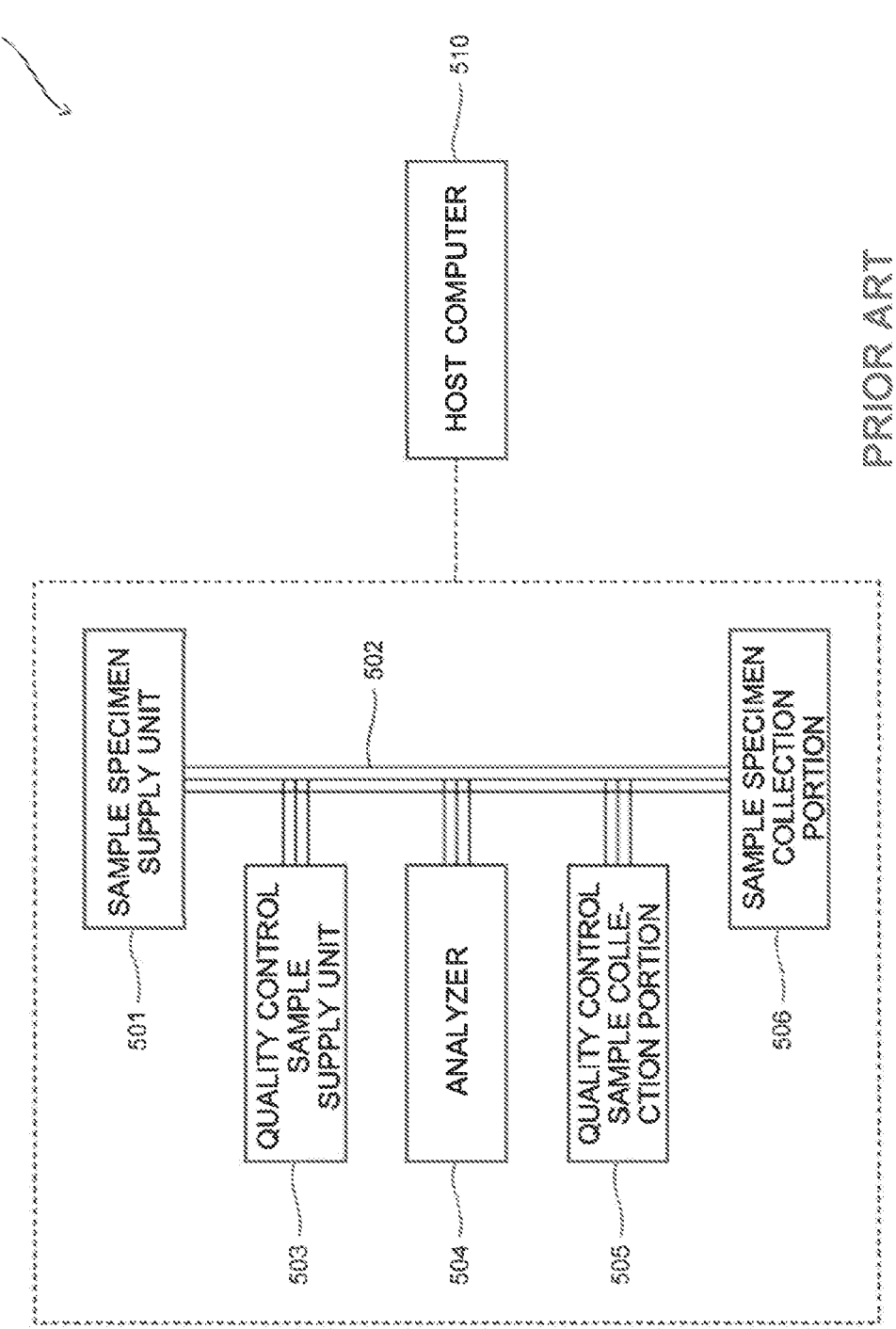
FIG. 19 is a schematic diagram illustrating a structure according to related art.

By the screen being shared, the staff member, in charge of the monitor, who operates the management apparatus 30 may determine that a reagent other than a genuine reagent is likely to have been used when the scattergram 340 in which the width in the vertical direction is small as shown in FIG. 17B is displayed on the display unit 40 instead of the scattergram 340 in which the width in the vertical direction is normal as shown in FIG. 17A being displayed. Thus, when a staff member in charge of the monitor suspects abnormality in quality control to have occurred, the screen is shared, whereby the staff member is allowed to know the state of the analyzer 20 in more detail.

When the controller 31 of the management apparatus 30 determines that abnormality in quality control has occurred, based on the second quality control information, the controller 31 may transmit, to the analyzer 20, a signal for requesting information for displaying a result of analysis of a specimen used for generating the second quality control information. In this case, the analyzer 20 reads, from the storage unit 62, the measurement data obtained by measuring the specimen used for generating the second quality control information, and transmits the read measurement data to the management apparatus 30. The measurement data other than information for identifying the subject is transmitted to the management apparatus 30.

When the management apparatus 30 receives the measurement data from the analyzer 20, the management apparatus 30 generates the scattergram 340 as the analysis result based on the received measurement data, and displays the generated scattergram 340 on the display unit 40. Thus, the staff member in charge of the monitor is allowed to determine whether or not the reagent is abnormal, that is, whether or not a reagent other than a genuine reagent is used, by referring to the scattergram 340 displayed on the display unit 40.

When the management apparatus 30 generates the scattergram 340 based on the received measurement data, the management apparatus 30 may determine whether or not a reagent other than a genuine reagent is used in the target analyzer 20 by further determining whether or not the particle distribution on the scattergram 340 is vertically compressed. Thus, whether or not a reagent other than a genuine reagent is used can be automatically determined. When the determination result is displayed on the display unit 40, the staff member in charge of the monitor is allowed to visually and quickly recognize abnormality in the reagent. The controller 31 may determine whether or not the fluorescence intensity in the particle distribution is reduced so as to compress the particle distribution by performing data processing of the measurement data without generating the scattergram 340 from the received measurement data. The controller 31 may receive only an image of the scattergram 340 based on the measurement data instead of receiving the measurement data from the analyzer 20.

What is claimed is:

1. An abnormality detection method for an analyzer measuring a specimen mixed with a reagent, comprising
    detecting abnormality of the analyzer, the reagent, or an artificially generated quality control substance, based on first quality control information obtained by measuring the quality control substance, and second quality control information obtained by measuring a plurality of specimens; and
    determining a cause of the abnormality based on the first quality control information and the second quality control information,
    wherein the detecting comprises judging whether the second quality control information has changed more than predetermined amount between before and after a change of a lot of the reagent, and
    wherein determining the cause of the abnormality comprises determining that the cause is an abnormality of the reagent in response to the second quality control information having changed more than the predetermined amount between before and after the change of the lot of the reagent.
2. The abnormality detection method of claim 1, wherein the detecting comprises:
    judging whether the first quality control information matches a first condition for abnormality detection;
    judging whether the second quality control information matches a second condition for abnormality detection; and
    detecting the abnormality of the analyzer, the reagent, or the quality control substance when the first quality control information matches the first condition for abnormality detection and/or the second quality control information matches the second condition for abnormality detection.
3. The abnormality detection method of claim 2, wherein the judging whether the second quality control information matches the second condition for abnormality detection comprises
    determining that the second quality control information matches the second condition when the second quality control information is outside of a variation range.
4. The abnormality detection method of claim 3, wherein determining that the second quality control information matches the second condition when a predetermined number of the second quality control information is continuously outside of the variation range.
5. The abnormality detection method of claim 2, wherein the judging whether the second quality control information matches the second condition for abnormality detection comprises
    determining that the second quality control information matches the second condition when a predetermined number of the second quality control information continuously ascends or descends.
6. The abnormality detection method of claim 1, further comprising
    determining a cause of the abnormality of the analyzer, the reagent, or the quality control substance.
7. The abnormality detection method of claim 6, wherein the detecting comprises:
    judging whether the first quality control information matches a first condition for abnormality detection; and
    judging whether the second quality control information matches a second condition for abnormality detection; and
    determining the cause of the abnormality comprises
    determining that the cause is abnormality of the analyzer or the reagent when the first quality control information does not match the first condition for abnormality detection and the second quality control information matches the second condition for abnormality detection.
8. The abnormality detection method of claim 7, wherein determining that the cause is abnormality of the reagent when the first quality control information does not match the first condition for abnormality detection and the second quality control information matches the second condition for abnormality detection.
9. The abnormality detection method of claim 6, wherein the detecting comprises:
    judging whether the first quality control information matches a first condition for abnormality detection; and
    judging whether the second quality control information matches a second condition for abnormality detection; and
    determining cause of the abnormality comprises
    determining that the cause is abnormality of the quality control substance when the first quality control information matches the first condition for abnormality detection and the second quality control information does not match the second condition for abnormality detection.
10. The abnormality detection method of claim 1, wherein the second quality control information comprises statistical information obtained by statistical processing of a plurality of measurement results of the plurality of specimens.
11. The abnormality detection method of claim 10, wherein
    the analyzer comprises an optical flow cytometer,
    the plurality of measurement results includes intensities of light obtained by measuring the plurality of specimens, and
    the statistical information is obtained by statistical processing of intensities of light which are obtained by measuring the plurality of specimens by the flow cytometer.

12. The abnormality detection method of claim 11, wherein
the plurality of measurement results further includes particle count values, for each kind of particle in the plurality of specimens, which is calculated based on the intensities of the light,
the statistical information includes first statistical information obtained by statistical processing of the intensities of the light and second statistical information obtained by statistical processing of the particle count values.

13. The abnormality detection method of claim 12, wherein
the detecting comprises:
judging whether the second statistical information matches a condition for abnormality detection; and
detecting the abnormality of the analyzer, the reagent, or the quality control substance when the second statistical information matches the condition for abnormality detection.

14. The abnormality detection method of claim 11, wherein
the plurality of specimens are stained by a dye from which fluorescence is generated by excitation light, and
the intensities of the light represents intensities of the fluorescence generated from the dye by which the plurality of specimens is stained.

15. The abnormality detection method of claim 1, further comprising
obtaining the first quality control information and the second quality control information from the analyzer via a network.

16. The abnormality detection method of claim 15, wherein
the network comprises an internet.

17. The abnormality detection method of claim 1, wherein the analyzer is a hematology analyzer.

18. The abnormality detection method of claim 1, further comprising
outputting the detected abnormality.

19. The abnormality detection method of claim 1, wherein determining the cause of the abnormality comprises determining that the cause is abnormality of the reagent when the first quality control information has not changed more than the predetermined amount between before and after the change of the lot of the reagent and the second quality control information has changed more than the predetermined amount between before and after the change of the lot of the reagent.

20. The abnormality detection method of claim 1, wherein the abnormality of the reagent indicates a use of non-genuine reagent.

21. A management apparatus connected to an analyzer measuring a specimen mixed with a reagent, comprising:
at least one processing device configured to:
detect abnormality of the analyzer, the reagent, or an artificially generated quality control substance, based on first quality control information obtained by measuring the quality control substance, and second quality control information obtained by measuring a plurality of specimens; and
determine a cause of the abnormality based on the first quality control information and the second quality control information,
wherein the detecting comprises judging whether the second quality control information has changed more than predetermined amount between before and after a change of a lot of the reagent, and
wherein determining the cause of the abnormality comprises determining that the cause is an abnormality of the reagent in response to the second quality control information having changed more than the predetermined amount between before and after the change of the lot of the reagent.

22. An abnormality detection system, comprising:
an analyzer measuring a specimen mixed with a reagent; and
a management apparatus connected to the analyzer, comprising at least one processing device configured to:
detect abnormality of the analyzer, the reagent, or an artificially generated quality control substance, based on first quality control information obtained by measuring the quality control substance, and second quality control information obtained by measuring a plurality of specimens; and
determining a cause of the abnormality based on the first quality control information and the second quality control information,
wherein the detecting comprises judging whether the second quality control information has changed more than predetermined amount between before and after a change of a lot of the reagent, and
wherein determining the cause of the abnormality comprises determining that the cause is an abnormality of the reagent in response to the second quality control information having changed more than the predetermined amount between before and after the change of the lot of the reagent.

* * * * *